(12) United States Patent (10) Patent No.: US 9,127,284 B2
Huang et al. (45) Date of Patent: Sep. 8, 2015

(54) MODIFIED BACTERIA AND THEIR USES THEREOF FOR THE TREATMENT OF CANCER OR TUMOR

(71) Applicant: The University of Hong Kong, Hong Kong (CN)

(72) Inventors: Jian-dong Huang, Hong Kong (CN); Bin Yu, Hong Kong (CN); Mei Yang, Hong Kong (CN); Lei Shi, Hong Kong (CN)

(73) Assignee: The University of Hong Kong, Hong Kong (CN)

( * ) Notice: Subject to any disclaimer, the term of this patent is extended or adjusted under 35 U.S.C. 154(b) by 0 days.

(21) Appl. No.: 13/871,716

(22) Filed: Apr. 26, 2013

(65) Prior Publication Data
US 2013/0295054 A1 Nov. 7, 2013

Related U.S. Application Data

(60) Provisional application No. 61/687,975, filed on May 4, 2012.

(51) Int. Cl.
| | | |
|---|---|---|
| *C12N 1/20* | (2006.01) | |
| *C12N 1/00* | (2006.01) | |
| *C12N 15/00* | (2006.01) | |
| *A01N 63/00* | (2006.01) | |
| *A61K 48/00* | (2006.01) | |
| *C12N 15/74* | (2006.01) | |
| *C12N 15/70* | (2006.01) | |
| *C12R 1/19* | (2006.01) | |
| *A61K 35/74* | (2015.01) | |
| *A61K 39/00* | (2006.01) | |
| *A61K 38/00* | (2006.01) | |

(52) U.S. Cl.
CPC ............... *C12N 15/74* (2013.01); *A61K 35/74* (2013.01); *C12N 15/70* (2013.01); *C12R 1/19* (2013.01); *A61K 38/00* (2013.01); *A61K 39/00* (2013.01)

(58) Field of Classification Search
CPC .......... C12N 15/70; C12R 1/19; A61K 38/00; A61K 39/00
See application file for complete search history.

(56) References Cited

U.S. PATENT DOCUMENTS

| 7,354,592 B2 | 4/2008 | Bermudes et al. |
| 7,514,089 B2 | 4/2009 | Bermudes et al. |
| 7,998,461 B2 | 8/2011 | Forbes et al. |
| 2003/0175297 A1 | 9/2003 | Urashima |
| 2006/0140975 A1 | 6/2006 | Curtiss, III et al. |
| 2009/0208534 A1 | 8/2009 | Xu et al. |
| 2010/0135973 A1 | 6/2010 | Eisenstark et al. |

OTHER PUBLICATIONS

Wei et al., European Journal of Cancer, 2007; 43: 490-496.*
Mengesha et al., Cancer Biology and Therapy, 2006; 5(9): 1120-1128.*
Hoiseth SK, Stocker BA., "Aromatic-dependent *Salmonella typhimurium* are non-virulent and effective as live vaccines," *Nature*, 1981, vol. 291(5812): pp. 238-239.
Jin Y, et al., "Small noncoding RNA GcvB is a novel regulator of acid resistance in *Escherichia coli.*," *BMC Genomics*, 2009, vol. 10:165: pp. 1471-2164.
Yu, B, et al., "A method to generate recombinant *Salmonella typhi* Ty21 a strains expressing multiple heterologous genes using an improved recombineering strategy," *Appl Microbiol Biotechnol.*, 2011, vol. 91(1): pp. 177-188.
Datta S, et al., "A set of recombineering plasmids for gram-negative bacteria," *Gene.*, 2006, vol. 1, 379: pp. 109-115.
Brown, J.M. and W.R. Wilson, "Exploiting tumour hypoxia in cancer treatment.," *Nat Rev Cancer*, 2004, vol. 4(6): pp. 437-447.
Zhou, J., et al.,"Tumor hypoxia and cancer progression," *Cancer Lett*, 2006. vol. 237(1): pp. 10-21.
Pawelek, J., K. Low, and D. Bermudes, "Bacteria as tumour-targeting vectors," *Lancet Oncol*, 2003, vol. 4: pp. 548-556.
St Jean, A.T., M. Zhang, and N. S. Forbes, "Bacterial therapies: completing the cancer treatment toolbox," *Curr Opin Biotechnol*, 2008, vol. 19(5): pp. 511-517.
Kasinskas, R.W. and N.S. Forbes, "*Salmonella typhimurium* specifically chemotax and proliferate in heterogeneous tumor tissue in vitro," *Biotechnol Bioeng.*, 2006. vol. 94(4): pp. 710-21.
Wei, M.Q., et al., "Clostridial spores as live 'Trojan horse' vectors for cancer gene therapy: comparison with viral delivery systems," *Genet Vaccines Ther.*, 2008. vol. 6: p. 8.
Kong, W., et al., "Regulated programmed lysis of recombinant *Salmonella* in host tissues to release protective antigens and confer biological containment," *PNAS*, 2008, vol. 105(27): pp. 9361-9366.
Wei, M.Q., et al., "Facultative or obligate anaerobic bacteria have the potential for multimodality therapy of solid tumours," *Eur J Cancer*, 2007, vol. 43(3): pp. 490-496.

(Continued)

*Primary Examiner* — Gary Nickol
*Assistant Examiner* — Lakia Tongue
(74) *Attorney, Agent, or Firm* — Leason Ellis LLP

(57) ABSTRACT

Described herein is a method of treatment of cancer or tumor using a modified bacteria or composition comprising the modified bacteria. In certain embodiments, the method is in combination with other treatment. In certain embodiments, the treatment is chemotherapy, radiation therapy, gene therapy, surgery or a combination thereof. The method makes modified facultative anaerobic bacteria into a conditional obligate anaerobe. The modified bacteria are strictly hypoxia regulated and comprise an essential gene expressing cassette. The vectors of this method comprise the essential gene expressing cassette. Also described herein are therapeutic and prophylactic compositions comprising the modified bacteria. The therapeutic and prophylactic compositions contain a purified form of the modified bacteria, while in certain embodiments, they do not contain other strain of microorganisms. The modified bacteria grow within the solid tumor/cancer, retarding its growth and are rapidly eliminated from normal tissues. The solid tumor/cancer includes breast cancer, liver cancer or neuroblastoma.

6 Claims, 25 Drawing Sheets

(56) References Cited

OTHER PUBLICATIONS

Figure 1A:
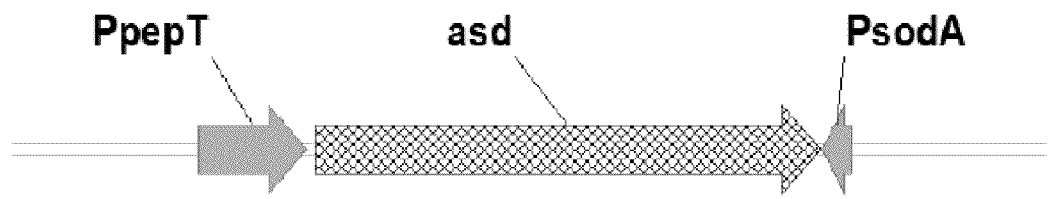

Dang, L.H., et al., "Combination bacteriolytic therapy for the treatment of experimental tumors," *Proc Natl Aced Sci U S A*, 2001, vol. 98(26): pp. 15155-15160.
Leschner, S. and S. Weiss, "*Salmonella*-allies in the fight against cancer," *J Mol Med*, 2010, vol. 88(8): pp. 763-773.
Sasaki, T., et al., "Genetically engineered *Bifidobacterium longum* for tumor-targeting enzyme-prodrug therapy of autochthonous mammary tumors in rats," *Cancer Sci*, 2006, vol. 97(7): pp. 649-657.
Yazawa, K., et al., "*Bifidobacterium longum* as a delivery system for cancer gene therapy: selective localization and growth in hypoxic tumors," *Cancer Gene Ther*, 2000, vol. 7(2): pp. 269-274.
Yazawa, K., et al., "*Bifidobacterium longum* as a delivery system for gene therapy of chemically induced rat mammary tumors," *Breast Cancer Res Treat*, 2001, vol. 66(2): pp. 165-170.
Barbe, S., L. Van Mellaert, and J. Anne, "The use of clostridial spores for cancer treatment," *J Appl Microbiol*, 2006, vol. 101(3): pp. 571-578.
Van Mellaert, L., S. Barbe, and J. Anne, "Clostridium spores as anti-tumour agents," *Trends Microbiol*, 2006. vol. 14(4): pp. 190-196.
Liu, S.C., et al., "Anticancer efficacy of systemically delivered anaerobic bacteria as gene therapy vectors targeting tumor hypoxia/necrosis," *Gene therapy*, 2002, vol. 9(4): pp. 291-296.
Theys, J., et al., "Repeated cycles of Clostridium-directed enzyme prodrug therapy result in sustained antitumour effects in vivo," *British journal of cancer*, 2006, vol. 95(9): pp. 1212-1219.
Liu, S.C., et al., "Optimized clostridium-directed enzyme prodrug therapy improves the antitumor activity of the novel DNA cross-linking agent PR-104," *Cancer research*, 2008, vol. 68(19): pp. 7995-8003.
Pawelek, J.M., K.B. Low, and D. Bermudes, "Tumor-targeted *Salmonella* as a novel anticancer vector," *Cancer Res*, 1997, vol. 57(20): pp. 4537-4544.
Low, K.B., et al., "Lipid a mutant *Salmonella* with suppressed virulence and TNFalpha induction retain tumor-targeting in vivo," *Nat Biotechnol*, 1999. vol. 17(1): pp. 37-41.
Kasinskas, R.W. and N.S. Forbes, "*Salmonella typhimurium* lacking ribose chemoreceptors localize in tumor quiescence and induce apoptosis," *Cancer Res*, 2007, vol. 67(7): pp. 3201-3209.
Nguyen, V.H., et al., "Genetically engineered *Salmonella typhimurium* as an imageable therapeutic probe for cancer," *Cancer Res*, 2010, vol. 70(1): pp. 18-23.
Zhao, M., et al., "Targeted therapy with a *Salmonella typhimurium* leucine-arginine auxotroph cures orthotopic human breast tumors in nude mice," *Cancer Res*, 2006, vol. 66(15): pp. 7647-7652.
Hayashi, K., et al., "Cancer metastasis directly eradicated by targeted therapy with a modified *Salmonella typhimurium*," *J Cell Biochem*, 2009. 106(6): p. 992-998.
Yam, C., et al., "Monotherapy with a Tumor-Targeting Mutant of *S. typhimurium* Inhibits Liver Metastasis in a Mouse Model of Pancreatic Cancer," *J Surg Res*, 2009.
Zhao, M., et al., "Monotherapy with a tumor-targeting mutant of *Salmonella typhimurium* cures orthotopic metastatic mouse models of human prostate cancer," *Proc Natl Aced Sci U S A*, 2007, vol. 104(24): pp. 10170-10174.
Hoiseth, S.K. and B.A. Stocker, "Aromatic-dependent *Salmonella typhimurium* are non-virulent and effective as live vaccines," *Nature*, 1981, vol. 291(5812): pp. 238-239.
Forbes, N.S., et al., "Sparse initial entrapment of systemically injected *Salmonella typhimurium* leads to heterogeneous accumulation within tumors," *Cancer Res*, 2003, vol. 63(17): pp. 5188-5193.
Leschner, S., et al., "Tumor invasion of *Salmonella enterica* serovar *Typhimurium* is accompanied by strong hemorrhage promoted by TNF-alpha," *PLoS One*, 2009, vol. 4(8): pp. e6692.
Loessner, H., et al., "Remote control of tumour-targeted *Salmonella enterica* serovar *Typhimurium* by the use of L-arabinose as inducer of bacterial gene expression in vivo," *Cell Microbiol*, 2007, vol. 9(6): pp. 1529-1537.

Royo, J.L., et al., "In vivo gene regulation in *Salmonella* spp. by a salicylate-dependent control circuit," *Nat Methods*, 2007. 4(11): pp. 937-942.
Westphal, K., et al., "Containment of tumor-colonizing bacteria by host neutrophil," *Cancer Res*, 2008, vol. 68(8): pp. 2952-2960.
Clairmont, C., et al., "Biodistribution and genetic stability of the novel antitumor agent VNP20009, a genetically modified strain of *Salmonella typhimurium*,"*J Infect Dis*, 2000. vol. 181(6): pp. 1996-2002.
Friedlos, F., et al., Attenuated *Salmonella* targets prodrug activating enzyme carboxypeptidase G2 to mouse melanoma and human breast and colon carcinomas for effective suicide gene therapy, *Clin Cancer Res*, 2008. vol. 14(13): pp. 4259-66.
Jia, L.J., et al., "Oral delivery of tumor-targeting *Salmonella* for cancer therapy in murine tumor models," *Cancer Sci*, 2007, vol. 98(7): p. 1107-1112.
Heimann, D.M. and S.A. Rosenberg, "Continuous intravenous administration of live genetically modified *salmonella typhimurium* in patients with metastatic melanoma," *Journal of immunotherapy*, 2003, vol. 26(2): pp. 179-180.
Toso, J.F., et al., "Phase I study of the intravenous administration of attenuated *Salmonella typhimurium* to patients with metastatic melanoma," *J Clin Oncol*, 2002, vol. 20(1): pp. 142-152.
Zhao, M., et al.,"Tumor-targeting bacterial therapy with amino acid auxotrophs of GFP-expressing *Salmonella typhimurium*," *Proc Natl Aced Sci USA*, 2005, vol. 102(3): pp. 755-760.
Song, M., et al., "ppGpp-dependent stationary phase induction of genes on *Salmonella* pathogenicity island 1," *J Biol Chem*, 2004, vol. 279(33): pp. 34183-34190.
Arrach, N., et al., "High-throughput screening for *Salmonella* avirulent mutants that retain targeting of solid tumors,"*Cancer Res*, 2010, vol. 70(6): pp. 2165-2170.
Crack, J., et al., "Influence of the Environment on the $[4Fe\text{—}4S]^{2+}$ to $[2Fe\text{—}2S]^{2+}$ Cluster Switch in the Transcriptional Regulator FNR," *J. Am. Chem. Soc.*, 2008, vol. 130: pp. 1749-1758.
Mengesha, A., et al., "Development of a Flexible and Potent Hypoxia-Inducible Promoter for Tumor-Targeted Gene Expression in Attenuated *Salmonella*,"*Cancer Biology & Therapy*, 2006, vol. 5(9): pp. 1120-1128.
Boysen, A., et al., "Translational regulation of gene expression by an anaerobically induced small non-coding RNA in *Escherichia coli.*," *J Biol Chem*, 2010, vol. 285(14): pp. 10690-10702.
Rainey, P.B. and G.M. Preston, "In vivo expression technology strategies: valuable tools for biotechnology," *Curr Opin Biotechnol*, 2000, vol. 11(5): pp. 440-444.
Zhang, N., et al., *Molecules*, 2008, vol. 13(8): pp. 1551-1569.
Clairmont, C., et al., "Biodistribution and genetic stability of the novel antitumor agent VNP20009, a genetically modified strain of *Salmonella typhimurium*," *J. Infect. Dis.*, 2000., vol. 181: pp. 1996-2000.
Toso, J., V. Gill, and P. Hwu, "Phase I study of the intravenous adminstration of attenuated *Salmonella typhimurium* to patients with metastatic melanoma,"*J. Clin. Oncol*, 2002. vol. 20: pp. 142-152.
Leschner, S. and S. Weiss, "*Salmonella*—allies in the fight against cancer," *J. Mol. Med.*, 2010. vol. 88: pp. 763-773.
Heap, J.T., et al., "The ClosTron: Mutagenesis in *Clostridium* refined and streamlined," *J Microbiol Methods*, 2010, vol. 80(1): pp. 49-55.
Yu, B., et al., A method to generate recombinant *Salmonella typhi* Ty21 a strains expressing multiple heterologous genes using an improved recombinant strategy, *Appl Microbiol Biotechnol.*, 2011, vol. 91: pp. 177-188.
Datta, S., N. Costantino, and D.L. Court, "A set of recombinant plasmids for gram-negative bacteria," *Gene*, 2006. vol. 379: pp. 109-115.
Man, K., et al., "Suppression of liver tumor growth and metastasis by adiponectin in nude mice through inhibition of tumor angiogenesis and downregulation of Rho kinase/IFN-inducible protein 10/matrix metalloproteinase 9 signaling," *Clin Cancer Res*, 2010, vol. 16: pp. 967-977.

* cited by examiner

```
  1  GTAAACGCAA CGGATGGCTG ACCGCTGCGG GGTTTGTGGT TAACCACCTT
 51  AATCACTCTT AATGAGGGCG GTCATTCTAC GGCAAACCAC CGTGATCGCC
101  AATCCTTGTT GCGAATTACT GACTTAGCTT TATAGTCAGA AAGCGTGTCA
151  AAGTGAAATA TTCTTGTTTG CAGGGATAAA AGTGACCTGA CGCAATATTT
201  GTCTTTTCTT GCTTATTAAT AATGTTGTCA CGAAAAG
```

Fig. 2A

```
   1  ATGAAAAATG TTGGTTTTAT CGGCTGGCGC GGAATGGTCG GCTCTGTTCT
  51  CATGCAACGC ATGGTAGAGG AGCGCGATTT CGACGCTATT CGCCCTGTTT
 101  TCTTTTCTAC CTCCCAGTTT GGACAGGCGG CGCCCACCTT CGGCGACACC
 151  TCCACCGGCA CGCTACAGGA CGCTTTTGAT CTGGATGCGC TAAAAGCGCT
 201  CGATATCATC GTGACCTGCC AGGGCGGCGA TTATACCAAC GAAATTTATC
 251  CAAAGCTGCG CGAAAGCGGA TGGCAGGGTT ACTGGATTGA CGCGGCTTCT
 301  ACGCTGCGCA TGAAAGATGA TGCCATTATT ATTCTCGACC CGGTCAACCA
 351  GGACGTGATT ACCGACGGAC TGAACAATGG CGTGAAGACC TTTGTGGGCG
 401  GTAACTGTAC CGTTAGCCTG ATGTTGATGT CGCTGGGCGG TCTCTTTGCC
 451  CATAATCTCG TTGACTGGGT ATCCGTCGCG ACCTATCAGG CCGCCTCCGG
 501  CGGCGGCGCG CGCCATATGC GCGAGCTGTT AACCCAAATG GGGCAGTTGT
 551  ATGGCCATGT CGCCGATGAA CTGGCGACGC CGTCTTCCGC AATTCTTGAT
 601  ATTGAACGCA AAGTTACGGC ATTGACCCGC AGCGGCGAGC TGCCGGTGGA
 651  TAACTTTGGC GTACCGCTGG CGGGAAGCCT GATCCCCTGG ATCGACAAAC
 701  AGCTTGATAA CGGCCAAAGC CGCGAAGAGT GGAAAGGCCA GGCGGAAACC
 751  AACAAGATCC TCAATACTGC CTCTGTGATC CCGGTTGATG GTTTGTGCGT
 801  GCGCGTCGGC GCGCTGCGCT GTCACAGCCA GGCGTTCACC ATTAAGCTGA
 851  AAAAAGAGGT ATCCATTCCG ACGGTGGAAG AACTGCTGGC GGCACATAAT
 901  CCGTGGGCGA AAGTGGTGCC GAACGATCGT GATATCACTA TGCGCGAATT
 951  AACCCCGGCG GCGGTGACCG GCACGTTGAC TACGCCGGTT GGTCGTCTGC
1001  GTAAGCTGAA CATGGGGCCA GAGTTCTTGT CGGCGTTTAC CGTAGGCGAC
1051  CAGTTGTTAT GGGGCGCCGC CGAGCCGCTG CGTCGAATGC TGCGCCAGTT
1101  GGCGTAG
```

Fig. 2B

```
  1  MKNVGFIGWR GMVGSVLMQR MVEERDFDAI RPVFFSTSQF GQAAPTFGDT
 51  STGTLQDAFD LDALKALDII VTCQGGDYTN EIYPKLRESG WQGYWIDAAS
101  TLRMKDDAII ILDPVNQDVI TDGLNNGVKT FVGGNCTVSL MLMSLGGLFA
151  HNLVDWVSVA TYQAASGGGA RHMRELLTQM GQLYGHVADE LATPSSAILD
201  IERKVTALTR SGELPVDNFG VPLAGSLIPW IDKQLDNGQS REEWKGQAET
251  NKILNTASVI PVDGLCVRVG ALRCHSQAFT IKLKKEVSIP TVEELLAAHN
301  PWAKVVPNDR DITMRELTPA AVTGTLTTPV GRLRKLNMGP EFLSAFTVGD
351  QLLWGAAEPL RRMLRQLA-
```

Fig. 2C

```
  1  ACGAAAAGTA CGGCATTGAT AATCATTTTC AATATCATTT AATTAACTAT
 51  AATGAACCAA
```

Fig. 2D

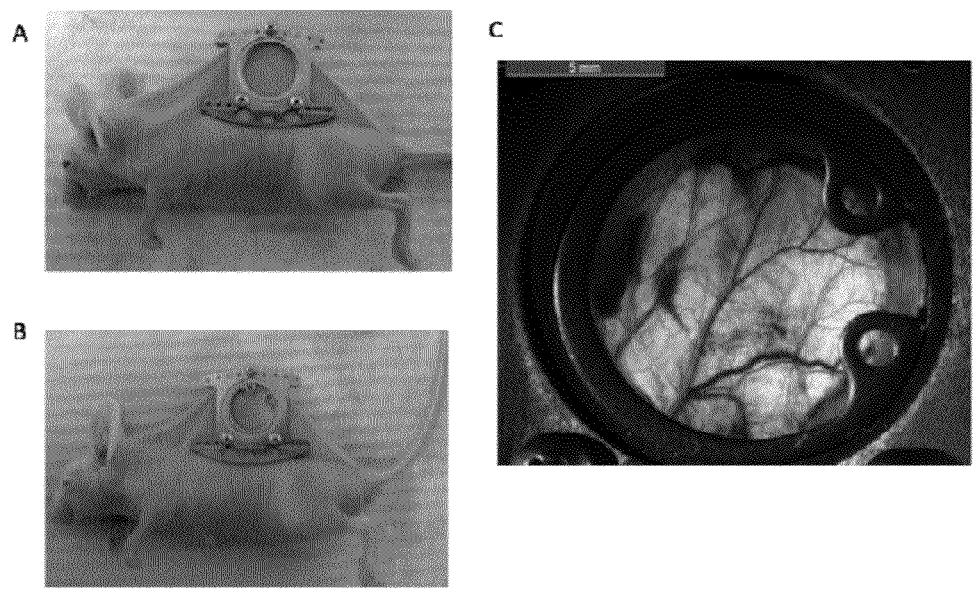
Figs. 15A-C

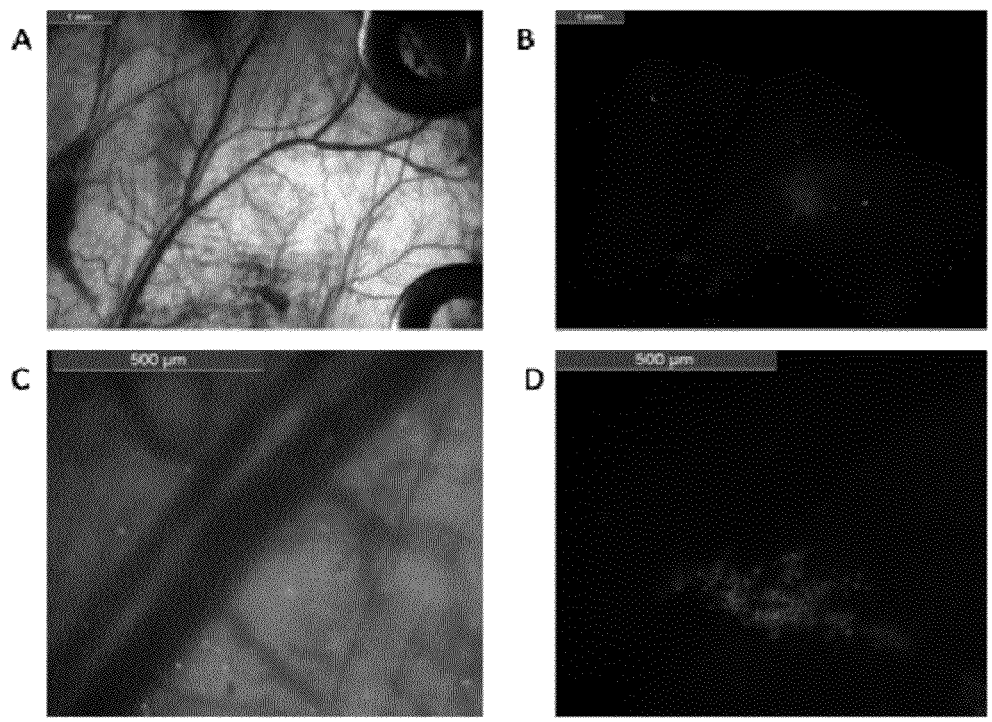
Figs. 16A-D

A
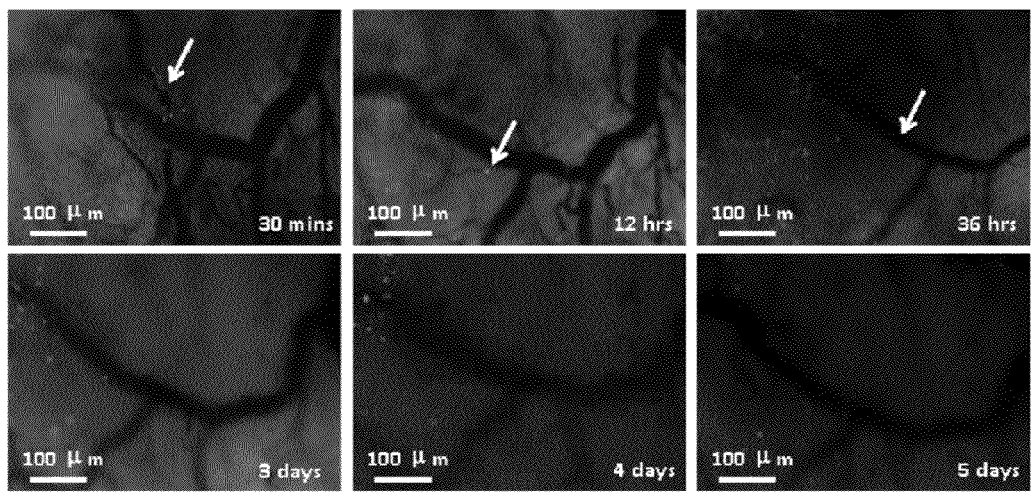
B
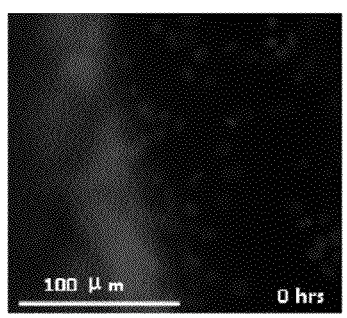
C
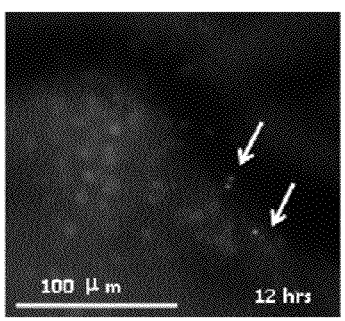
D
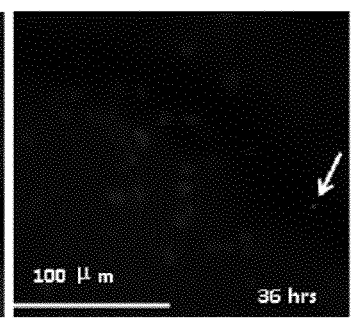
Figs. 17A-D

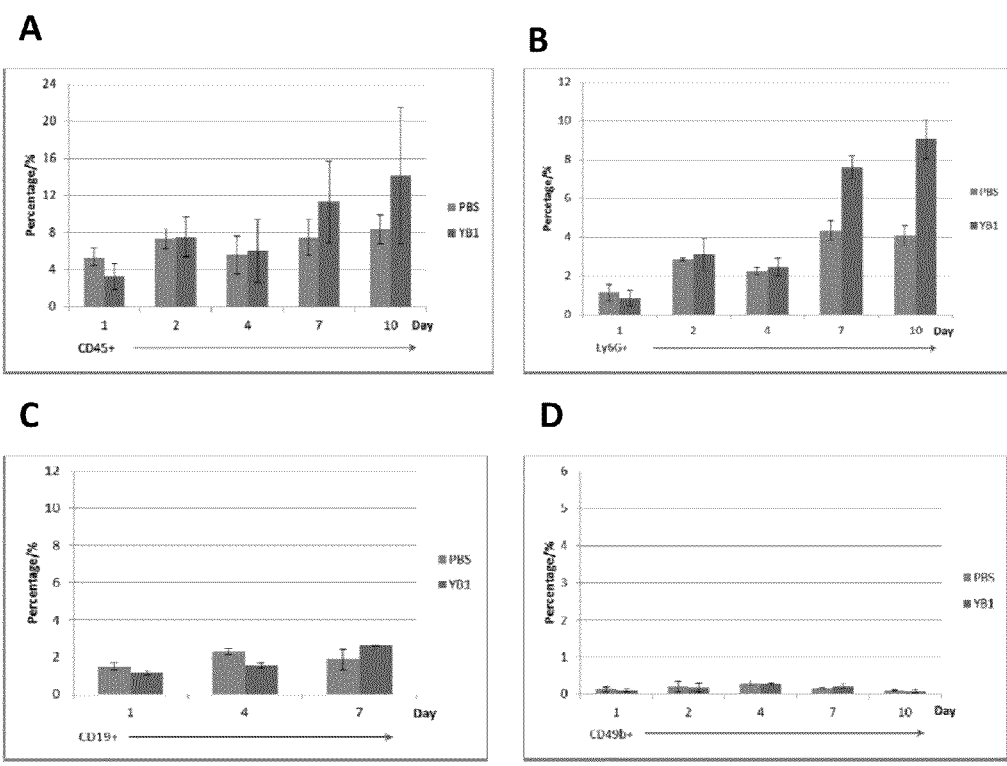
Figs. 18A-D

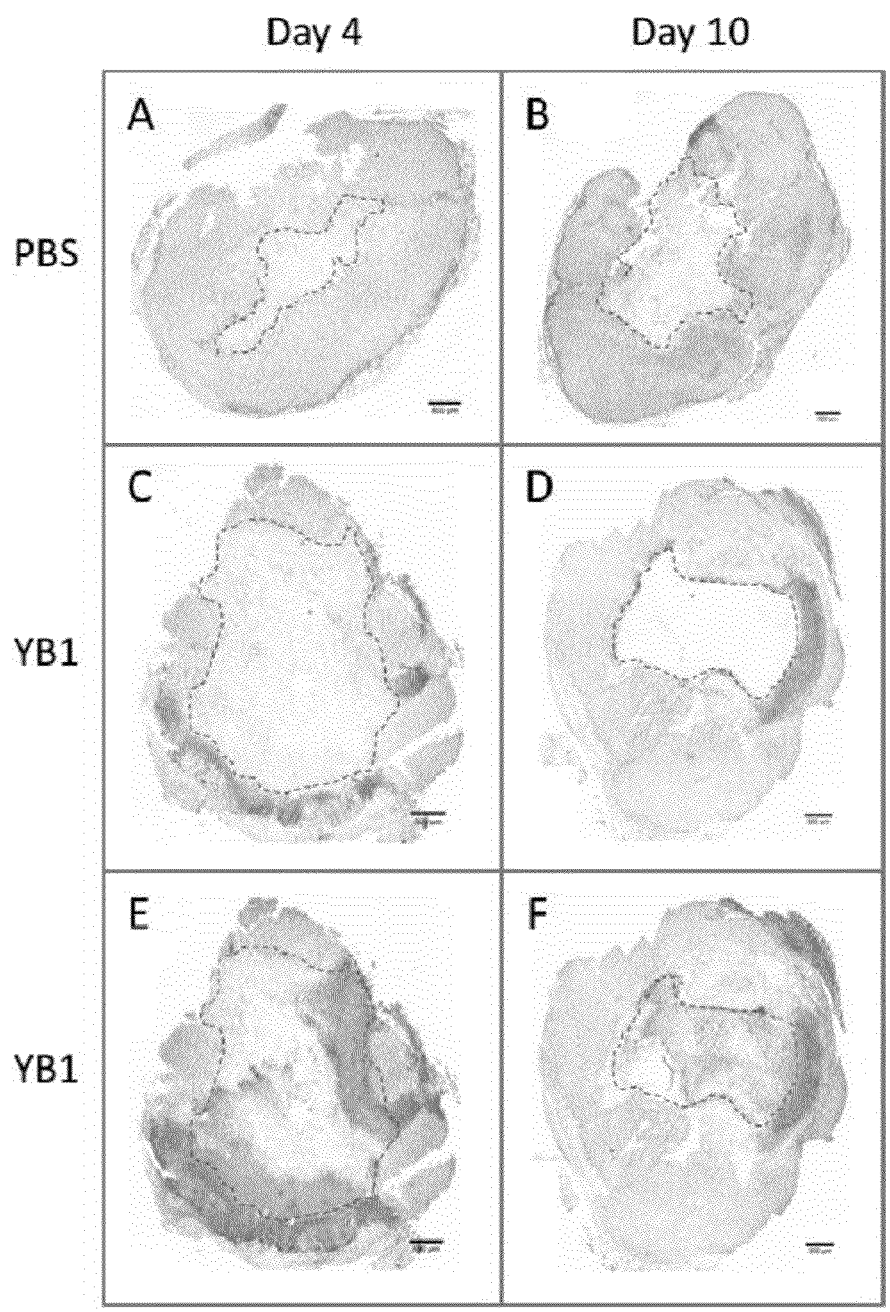
Figs. 19A-F

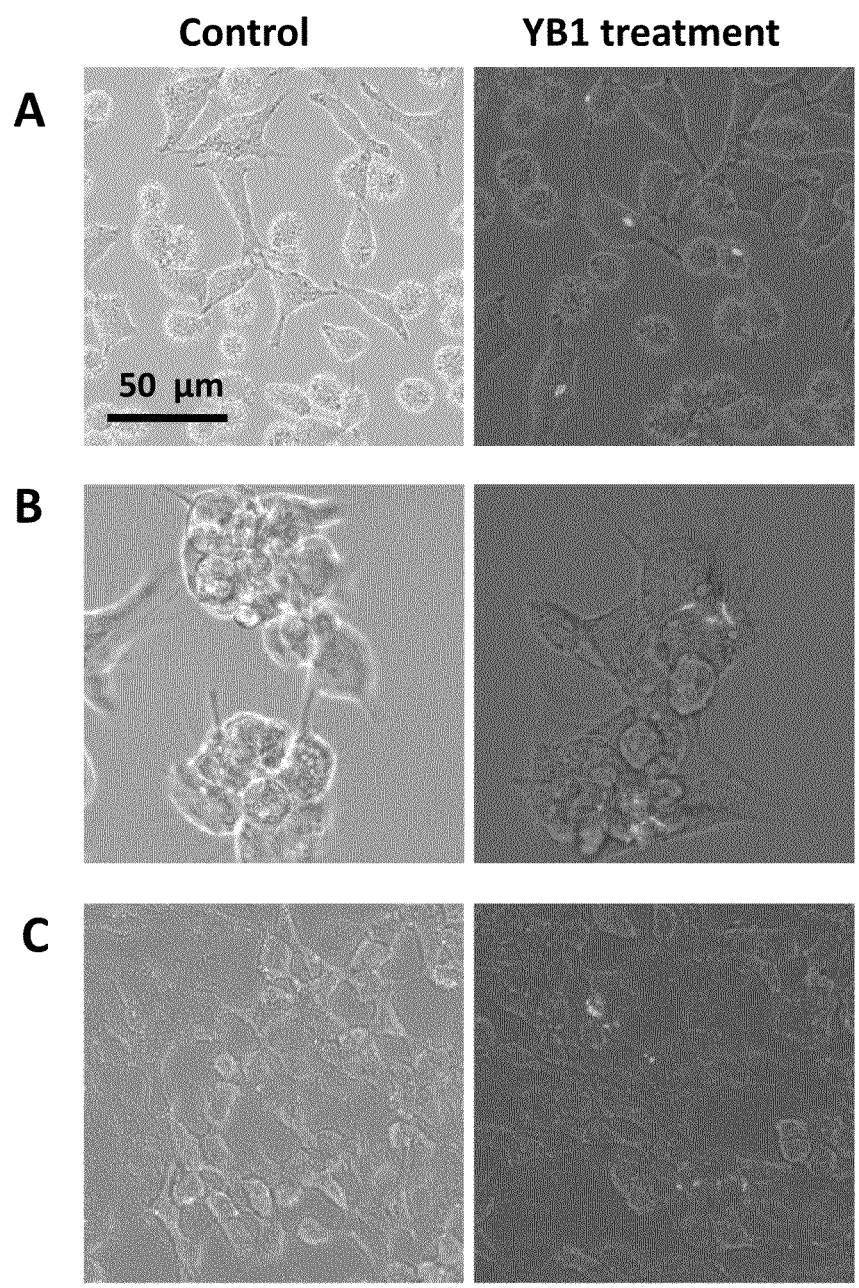
Figs. 21A-C

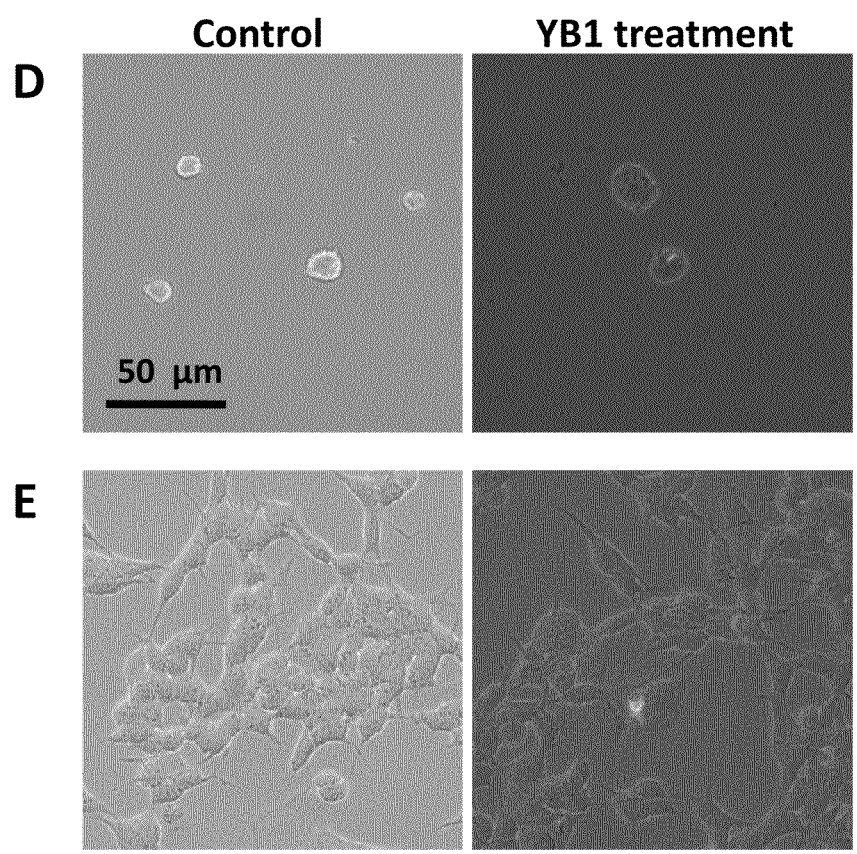
Figs. 21D-E

SEQUENCE LISTING

<160> NUMBER OF SEQ ID NOS: 21

<210> SEQ ID NO 1
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
atttgcggcc gcgtaaacgc aacggatggc tgaccgc                              37

<210> SEQ ID NO 2
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cccaagcttc ttttcgtgac aacattatta ataag                               35

<210> SEQ ID NO 3
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cccaagcttt ggagcgaaac cgatgaaaaa tgttggtttt atcggctggc               50

<210> SEQ ID NO 4
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ccgctcgagc tacgccaact ggcgcagcat tcga                                34

<210> SEQ ID NO 5
<211> LENGTH: 67
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ccgctcgagc tacagatctt cttcgctaat cagtttctgt tcttccgcca actggcgcag   60
cattcga                                                              67

<210> SEQ ID NO 6
<211> LENGTH: 69
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
atttgcggcc gcttttttga cctgcctcaa actttgtaga tctccaaaat atattcacgt    60
tgtaaattg    69

<210> SEQ ID NO 7
<211> LENGTH: 73
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cccaagcttc gctacgcatt atcccttagc tctgtatggg aaatttgacg ttaaacaatt    60
tacaacgtga ata    73

<210> SEQ ID NO 8
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gacgaaaagt acggcattga taatcatttt caatatcatt taattaacta taatgaacca    60
ac    62

<210> SEQ ID NO 9
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tcgagttggt tcattatagt taattaaatg atattgaaaa tgattatcaa tgccgtactt    60
ttcgtctgca    70

<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
atttgcggcc gcccgatcat attcaataac cct    33

<210> SEQ ID NO 11
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
atttgcggcc gcgactagtg aacctcttcg aggg    34

<210> SEQ ID NO 12
<211> LENGTH: 87

<212> TYPE: DNA
<213> ORGANISM: Artificial Sequence
<220> FEATURE:
<223> OTHER INFORMATION: Description of Artificial Sequence: Synthetic primer

<400> SEQUENCE: 12
gtatggtgaa ggatgcgcca caggatactg gcgcgcatac acagcacatc tctttgcagg    60
aaaaaaccga tcatattcaa taaccct    87

<210> SEQ ID NO 13
<211> LENGTH: 91
<212> TYPE: DNA
<213> ORGANISM: Artificial Sequence
<220> FEATURE:
<223> OTHER INFORMATION: Description of Artificial Sequence: Synthetic primer

<400> SEQUENCE: 13
atggcggcgc tgacgcgcct tatccggcct acagaaccac acgcaggccc gataagcgct    60
gcaatagccg actagtgaac ctcttcgagg g    91

<210> SEQ ID NO 14
<211> LENGTH: 73
<212> TYPE: DNA
<213> ORGANISM: Artificial Sequence
<220> FEATURE:
<223> OTHER INFORMATION: Description of Artificial Sequence: Synthetic primer

<400> SEQUENCE: 14
gctggcggcg gcagtgcgca tcattcaggg ttccgcgacc gtggcgtgtt agggttttcc    60
cagtcacgac gtt    73

<210> SEQ ID NO 15
<211> LENGTH: 74
<212> TYPE: DNA
<213> ORGANISM: Artificial Sequence
<220> FEATURE:
<223> OTHER INFORMATION: Description of Artificial Sequence: Synthetic primer

<400> SEQUENCE: 15
tgcaattagc gcattaatca cgtctctatc gatacgactg gacatggttt gagcggataa    60
caatttcaca cagg    74

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 16
gattctggtc gcttgtctgg    20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 17
acattccagt ttgccgactt                                                        20

<210> SEQ ID NO 18
<211> LENGTH: 237
<212> TYPE: DNA
<213> ORGANISM: Salmonella enterica

<400> SEQUENCE: 18
gtaaacgcaa cggatggctg accgctgcgg ggtttgtggt taaccacctt aatcactctt     60
aatgagggcg gtcattctac ggcaaaccac cgtgatcgcc aatccttgtt gcgaattact    120
gacttagctt tatagtcaga aagcgtgtca aagtgaaata ttcttgtttg cagggataaa    180
agtgacctga cgcaatattt gtcttttctt gcttattaat aatgttgtca cgaaaag      237

<210> SEQ ID NO 19
<211> LENGTH: 1107
<212> TYPE: DNA
<213> ORGANISM: Salmonella enterica

<400> SEQUENCE: 19
atgaaaaatg ttggttttat cggctggcgc ggaatggtcg gctctgttct catgcaacgc     60
atggtagagg agcgcgattt cgacgctatt cgccctgttt tcttttctac ctcccagttt    120
ggacaggcgg cgcccacctt cggcgacacc tccaccggca cgctacagga cgcttttgat    180
ctggatgcgc taaaagcgct cgatatcatc gtgacctgcc agggcggcga ttataccaac    240
gaaatttatc caaagctgcg cgaaagcgga tggcagggtt actggattga cgcggcttct    300
acgctgcgca tgaaagatga tgccattatt attctcgacc cggtcaacca ggacgtgatt    360
accgacggac tgaacaatgg cgtgaagacc tttgtgggcg gtaactgtac cgttagcctg    420
atgttgatgt cgctgggcgg tctctttgcc cataatctcg ttgactgggt atccgtcgcg    480
acctatcagg ccgcctccgg cggcggcgcg cgccatatgc gcgagctgtt aacccaaatg    540
gggcagttgt atggccatgt cgccgatgaa ctggcgacgc cgtcttccgc aattcttgat    600
attgaacgca agttacggc attgacccgc agcggcgagc tgccggtgga taactttggc    660
gtaccgctgg cgggaagcct gatcccctgg atcgacaaac agcttgataa cggccaaagc    720
cgcgaagagt ggaaaggcca gcggaaaacc aacaagatcc tcaatactgc ctctgtgatc    780
ccggttgatg gtttgtgcgt gcgcgtcggc gcgctgcgct gtcacagcca ggcgttcacc    840
attaagctga aaaagaggt atccattccg acggtggaag aactgctggc ggcacataat    900
ccgtgggcga aagtggtgcc gaacgatcgt gatatcacta tgcgcgaatt aaccccggcg    960
gcggtgaccg gcacgttgac tacgccggtt ggtcgtctgc gtaagctgaa catggggcca   1020
gagttcttgt cggcgtttac cgtaggcgac cagttgttat ggggcgccgc cgagccgctg   1080
cgtcgaatgc tgcgccagtt ggcgtag                                       1107

<210> SEQ ID NO 20
<211> LENGTH: 368
<212> TYPE: PRT
<213> ORGANISM: Salmonella enterica

<400> SEQUENCE: 20

Met Lys Asn Val Gly Phe Ile Gly Trp Arg Gly Met Val Gly Ser Val
1               5                   10                  15

Leu Met Gln Arg Met Val Glu Glu Arg Asp Phe Asp Ala Ile Arg Pro
            20                  25                  30

```
Val Phe Phe Ser Thr Ser Gln Phe Gly Gln Ala Ala Pro Thr Phe Gly
         35                  40                  45

Asp Thr Ser Thr Gly Thr Leu Gln Asp Ala Phe Asp Leu Asp Ala Leu
         50                  55                  60

Lys Ala Leu Asp Ile Ile Val Thr Cys Gln Gly Gly Asp Tyr Thr Asn
 65                  70                  75                  80

Glu Ile Tyr Pro Lys Leu Arg Glu Ser Gly Trp Gln Gly Tyr Trp Ile
                 85                  90                  95

Asp Ala Ala Ser Thr Leu Arg Met Lys Asp Asp Ala Ile Ile Ile Leu
                100                 105                 110

Asp Pro Val Asn Gln Asp Val Ile Thr Asp Gly Leu Asn Asn Gly Val
            115                 120                 125

Lys Thr Phe Val Gly Gly Asn Cys Thr Val Ser Leu Met Leu Met Ser
    130                 135                 140

Leu Gly Gly Leu Phe Ala His Asn Leu Val Asp Trp Val Ser Val Ala
145                 150                 155                 160

Thr Tyr Gln Ala Ala Ser Gly Gly Gly Ala Arg His Met Arg Glu Leu
                165                 170                 175

Leu Thr Gln Met Gly Gln Leu Tyr Gly His Val Ala Asp Glu Leu Ala
                180                 185                 190

Thr Pro Ser Ser Ala Ile Leu Asp Ile Glu Arg Lys Val Thr Ala Leu
                195                 200                 205

Thr Arg Ser Gly Glu Leu Pro Val Asp Asn Phe Gly Val Pro Leu Ala
    210                 215                 220

Gly Ser Leu Ile Pro Trp Ile Asp Lys Gln Leu Asp Asn Gly Gln Ser
225                 230                 235                 240

Arg Glu Glu Trp Lys Gly Gln Ala Glu Thr Asn Lys Ile Leu Asn Thr
                245                 250                 255

Ala Ser Val Ile Pro Val Asp Gly Leu Cys Val Arg Val Gly Ala Leu
                260                 265                 270

Arg Cys His Ser Gln Ala Phe Thr Ile Lys Leu Lys Lys Glu Val Ser
    275                 280                 285

Ile Pro Thr Val Glu Glu Leu Leu Ala Ala His Asn Pro Trp Ala Lys
    290                 295                 300

Val Val Pro Asn Asp Arg Asp Ile Thr Met Arg Glu Leu Thr Pro Ala
305                 310                 315                 320

Ala Val Thr Gly Thr Leu Thr Thr Pro Val Gly Arg Leu Arg Lys Leu
                325                 330                 335

Asn Met Gly Pro Glu Phe Leu Ser Ala Phe Thr Val Gly Asp Gln Leu
                340                 345                 350

Leu Trp Gly Ala Ala Glu Pro Leu Arg Arg Met Leu Arg Gln Leu Ala
    355                 360                 365

<210> SEQ ID NO 21
<211> LENGTH: 60
<212> TYPE: DNA
<213> ORGANISM: Escherichia coli

<400> SEQUENCE: 21
acgaaaagta cggcattgat aatcattttc aatatcattt aattaactat aatgaaccaa      60
```

MODIFIED BACTERIA AND THEIR USES THEREOF FOR THE TREATMENT OF CANCER OR TUMOR

CROSS-REFERENCE TO RELATED APPLICATION

The present application claims the benefit of U.S. provisional patent application Ser. No. 61/687,975, filed May 4, 2012, which is hereby incorporated by reference in its entirety.

SEQUENCE LISTING

The instant application contains a Sequence Listing which has been submitted in ASCII format via EFS-Web and is hereby incorporated by reference in its entirety. Said ASCII copy, created on Apr. 30, 2013, is named Sequence_Listing_002893-US1.txt and is 10,182 bytes in size.

1. INTRODUCTION

Described herein is a method of treatment of cancer or tumor using a modified bacteria or composition comprising the modified bacteria. In certain embodiments, the method of treatment of cancer or tumor is in combination with other cancer or tumor treatment. In certain embodiments, the cancer or tumor treatment is chemotherapy, radiation therapy, gene therapy, surgery or a combination thereof. Described herein is a method of making modified facultative anaerobic bacteria into a conditional obligate anaerobe. In one aspect, the modified bacteria are strictly hypoxia regulated and comprise an essential gene expressing cassette. Described herein are vectors, cells comprising the vectors comprising the essential gene expressing cassette. Also described herein are therapeutic and prophylactic compositions comprising the modified bacteria. In certain embodiments, the therapeutic and prophylactic compositions contain a purified form of the modified bacteria. In certain embodiments, the therapeutic and prophylactic compositions do not contain other strains of microorganisms. In one aspect, the modified bacteria grow within a tumor/cancer, retarding its growth. In one aspect, the tumor/cancer is a solid tumor/cancer. In one aspect, the modified bacteria are rapidly eliminated from normal tissues. In certain embodiments, the tumor/cancer includes, but is not limited to, breast cancer, liver cancer or neuroblastoma.

2. BACKGROUND

Cancer is one of the most deadly diseases in the present world. Facing cancer, most people believe surgery, chemotherapy or radiation therapy is the only possible solution. However, not all cancer patients are suitable for surgery, and cancer metastasis may cause the failure of surgery treatment. The chemotherapy or radiation therapy may lead to large damage of normal organs and less effect on cancer niche. Furthermore, hypoxic tumor cells may demonstrate an inhibition of cell cycle progression and proliferation, and hence may be relatively resistant to many anticancer drugs that target rapidly dividing cells. Thus, in solid tumors, hypoxic regions create a further problem as they are resistant to many treatments [1] and are linked to more malignant phenotypes [2].

Intentional use of bacteria in cancer treatment can be dated to the late 19th century with even earlier anecdotal reports of bacterial efficacy in treating cancer [3, 10, 11]. The first reported deliberate attempt at using bacteria (*Streptococcus pyogenes*) to treat an inoperable sarcoma also demonstrated the inherent danger of the technique. Whilst the tumor and lymph nodes reduced appreciably, the patient died of infection within 9 days of treatment [3, 10, 11]. On the other hand, targeted cancer therapy, gene therapy and cancer vaccine are all based on the transfection technique. The most critical issues associated with these therapeutic strategies are the safety of vectors. Viral vectors are most widely used delivery vectors, however, they are not easy to be eliminated, potentially tumorigenic with limited capacity. Accordingly, non-viral vectors with larger capacity and safe manipulation, such as bacterial vectors, are a promising approach to develop new delivery systems.

Consequently, much recent work on bacterial therapies for cancer has focused on non-pathogenic strains or the need to attenuate bacteria for use in model systems and humans. *Bifidobacteria* are non-pathogenic obligate anaerobes and have been successfully used to target tumors and as a therapeutic vectors but do not appear to have an oncolytic effect [8, 12-14].

3. SUMMARY

Described herein is a modified bacteria comprising a strictly hypoxia regulated essential gene expressing cassette. Also described herein is a composition comprising the modified bacteria. Also described herein are therapeutic and prophylactic compositions comprising the modified bacteria. In certain embodiments, the therapeutic and prophylactic compositions contain a purified form of the modified bacteria. In certain embodiments, the therapeutic and prophylactic compositions do not contain other strains of microorganisms.

Provided herein is a strictly hypoxia regulated cassette comprising a forward anaerobic inducible promoter, an essential gene and a reverse aerobic promoter.

Described herein are vectors, cells comprising the vectors. In certain embodiments, the vectors comprise the essential gene expressing cassette. Described herein is a vector comprising a hypoxia conditioned promoter operatively linked to an essential gene. In one embodiment, the hypoxia conditioned promoter comprises an inducer binding site. In one embodiment, the vector further comprises an antisense promoter that is negatively regulated by the inducer.

Described herein is a method of making the modified bacteria. Also described herein is a method of making modified facultative anaerobic bacteria into a conditional obligate anaerobe. In one aspect, the modified bacteria are strictly hypoxia regulated and comprise an essential gene expressing cassette.

Also described herein is a method of treatment of cancer using a modified bacteria or a composition comprising the modified bacteria. The method inhibits and reduces the growth of a tumor cancer when administered in vivo. In certain embodiments, the method of treatment of cancer is in combination with other cancer treatment. In certain embodiments, the cancer or tumor treatment is chemotherapy, radiation therapy, gene therapy, surgery or a combination thereof. In one aspect, the modified bacteria grow within the solid tumor/cancer, retarding its growth. In one aspect, the modified bacteria are rapidly eliminated from normal tissues. In certain embodiments, the solid tumor/cancer includes, but is not limited to, breast cancer, liver cancer or neuroblastoma.

Also described herein is a kit comprising the modified bacteria and a pharmaceutically acceptable carrier.

Described herein is a method to provide an obligate anaerobe from a facultative anaerobe. In another embodiment, the facultative anaerobic is a Gram-negative bacteria. In certain embodiments, the facultative anaerobic, includes, but not limited to *Salmonella typhimurium*. In certain embodiments, the modified bacteria are effective in anti-tumor therapy. In certain embodiment, the essential gene is, for example, a gene for aspartate-semialdehyde dehydrogenase ("asd"). In certain embodiments, asd is operatively linked and is under the control of a hypoxia-conditioned promoter. In certain embodiments, the normal functions of the bacteria are not compromised by the deletion or mutation of any of its genes.

In one embodiment, the modified bacteria are YB1. Comparison of the new strain YB1 with previously studied tumor-targeting *Salmonella* strain VNP20009 shows that YB1 is more effective in both targeting and repressing tumor growth than VNP20009. Furthermore, YB1 was eliminated from normal tissues much faster than VNP20009 in breast cancer animal model. In one embodiment, the modified bacteria are not VNP20009.

In one embodiment, the modified bacteria are not viable in normal tissues. In one embodiment, the modified bacteria are made by placing an essential gene, asd, under the control of a hypoxia-induced promoter. In one embodiment, the essential gene is asd or diaminopimelic acid ("dapA"). The asd gene of *Salmonella* encodes an enzyme essential for the synthesis of diaminopimelic acid (DAP), which is an essential component of the bacterial cell wall and not present in mammalian systems [7]. In one embodiment, with asd expressed only in hypoxic conditions the bacteria are able to grow readily under hypoxia, but will lyse under normal growth conditions. Thus in certain embodiments, facultative anaerobic Gram-negative bacteria, including, *Salmonella typhi*, can be converted from a facultative to an "obligate" anaerobe, rendering it safe in normal tissues. In certain embodiments, the modified bacteria are *Salmonella typhimurium, Salmonella choleraesuis, Salmonella enteritidis* and *S. typhimurium, Escherichia coli, Escherichia coli K-12, Escherichia coli O157:H7, Shigella, Shigella dysenteriae, Shigella flexneri, Shigella boydii, Shigella sonnei, Yersinia, Yersinia pestis, Yersinia pseudotuberculosis* and *Yersina enterocolitica*.

Figure 5:
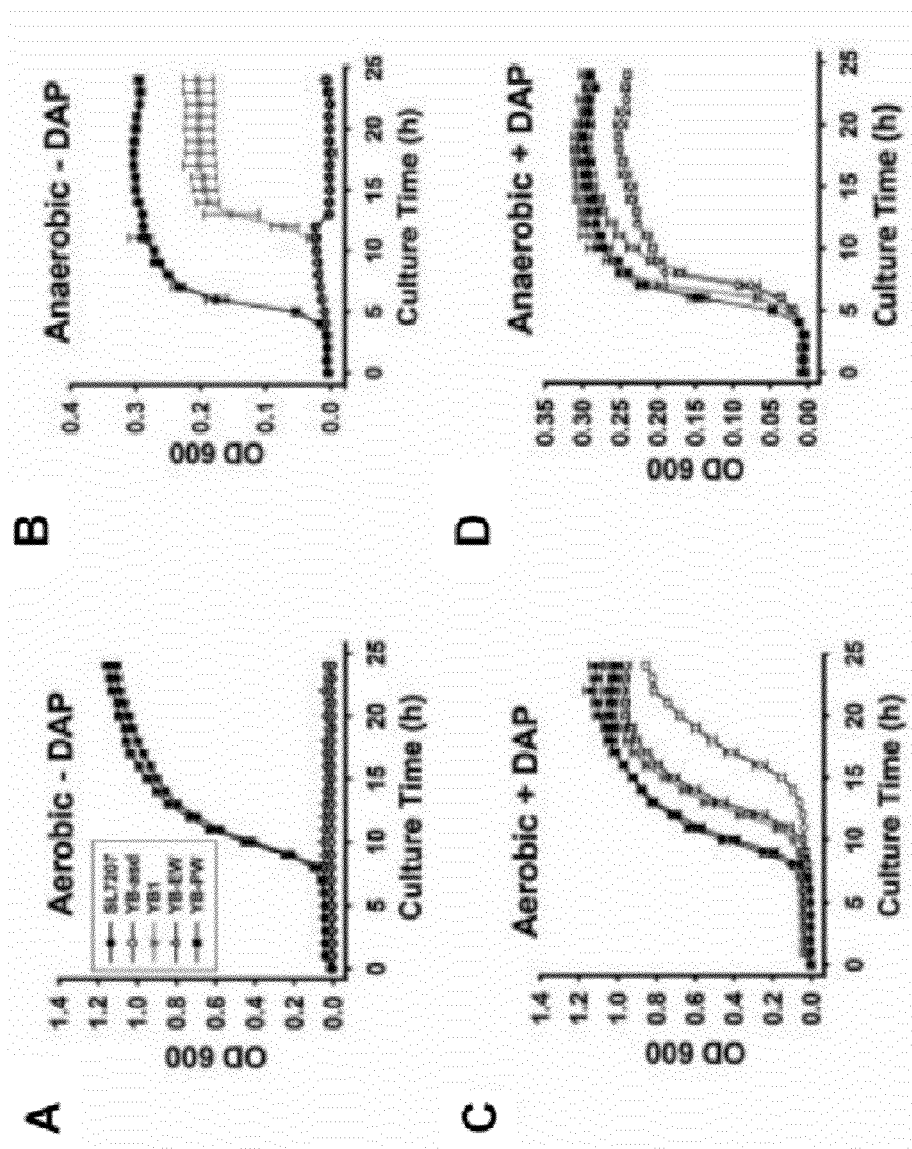
Figure 6:
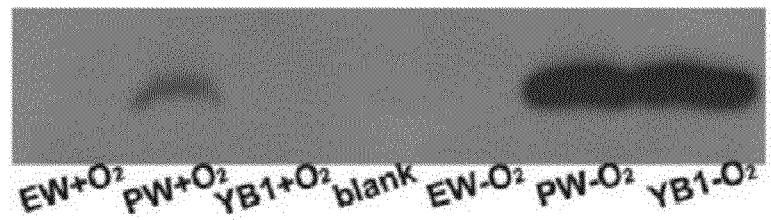
Figure 7:
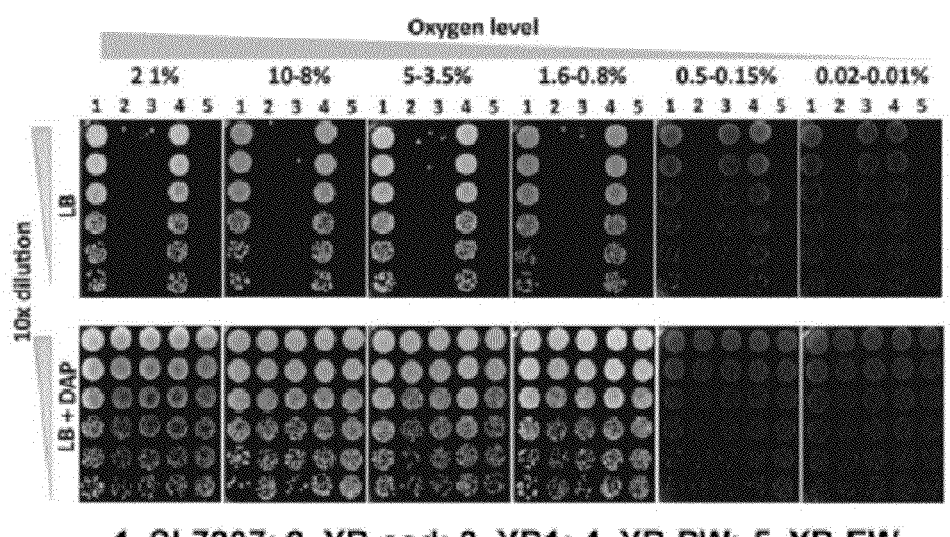

In one embodiment, a cassette described herein is regulated by fumarate and nitrate reduction gene ("fnr") which are involved in the switch between aerobic and anaerobic growth [42]. Promoters containing FNR binding sites are activated under hypoxia [43]. Provided herein, in an embodiment, the pepT promoter created a gene therapy vector only expressed in hypoxic regions [43]. In certain embodiments, the pepT promoter (PpepT) was used to drive expression of asd, conditional on hypoxia, in a modified *Salmonella* SL7207 (YB-pw), limiting the bacterial viability to hypoxic regions. In an embodiment, the asd gene in the modified bacteria was replaced with a PpepT-asd construct (FIG. 1B). In certain embodiment, the essential gene is under the control of L-asparaginase II ("ansB") or formate dehydrogenase-II ("fdhF") promoter. However, in certain embodiment, the modified bacteria are still able to grow under normal oxygen levels. In one embodiment, to prevent leakage from the pepT promoter, an antisense promoter of the superoxide dismutase ("sodA") gene (PsodA), which is negatively regulated by FNR [44], was added to the PpepT-asd construct to make the PpepT-asd-sodA (FIG. 1A), which then further constructed strain YB1. This effectively inhibited the growth of *Salmonella* as shown in FIG. 5-7 where YB1 could only grow in the absence of DAP under anaerobic but not under aerobic conditions. An alternate construct using the ansB promoter (YB-EW) is ineffective under anaerobic conditions. In the absence of DAP, YB1 was the only strain that had the combination of growth under anaerobic but not aerobic conditions. A detailed titration of oxygen level and bacterial concentration showed that, in the absence of DAP, YB1 was only viable at oxygen levels below 0.5% (FIG. 7). Unlike SL7207, YB1 only infiltrated the MDA-MB-231 breast cancer cells under anaerobic conditions. However, it was more effective at inducing apoptosis or cell death, possibly due to the anaerobic expression of asd being stronger under the hypoxia conditioned promoter as compared to the wild type one (FIG. 4).

Certain embodiments shows SL7207, YB1 and an attenuated *Salmonella* strain VNP20009 were able to infiltrate MDA-MB-231 tumors induced in nude mice, as evidenced by the considerable number of bacteria found in the tumor and the considerable tumor damage observed. Although quiescent YB1 cells appear to persist briefly in aerobic tissues in the absence of DAP [45], YB1 was effectively cleared from normal tissues. By 3 days post infection, bacteria were barely detectable in liver. VNP20009 was less effectively cleared from normal tissues than YB1 and less effective at reducing tumor size. SL7207, despite being an attenuated vaccine strain, had a similar effect on normal and tumor cells and killed all mice by 11 days post infection with substantial bacterial induced liver destruction apparent. While SL7207 might not affect immuno-competent mice, the conversion of SL7207 to the "obligate" anaerobic YB1 prevented bacterial killing of the mice while maintaining and enhancing tumor killing ability.

Described herein is an examination of the effect of YB1 in tumors. The examination showed that its design as an "obligate" anaerobe was effective in that it was tightly confined to the hypoxic regions of tumors and kept distant from blood vessels. As bacteria are expected to induce a host immune response, neutrophils were found in the YB1 infected tumors. In one embodiment, YB1 and neutrophils aligned against each other with neutrophils as a barrier against further bacterial spread. In one embodiment, YB1 enhances tumor killing by strongly attracting neutrophils to the tumor.

Figure 13:
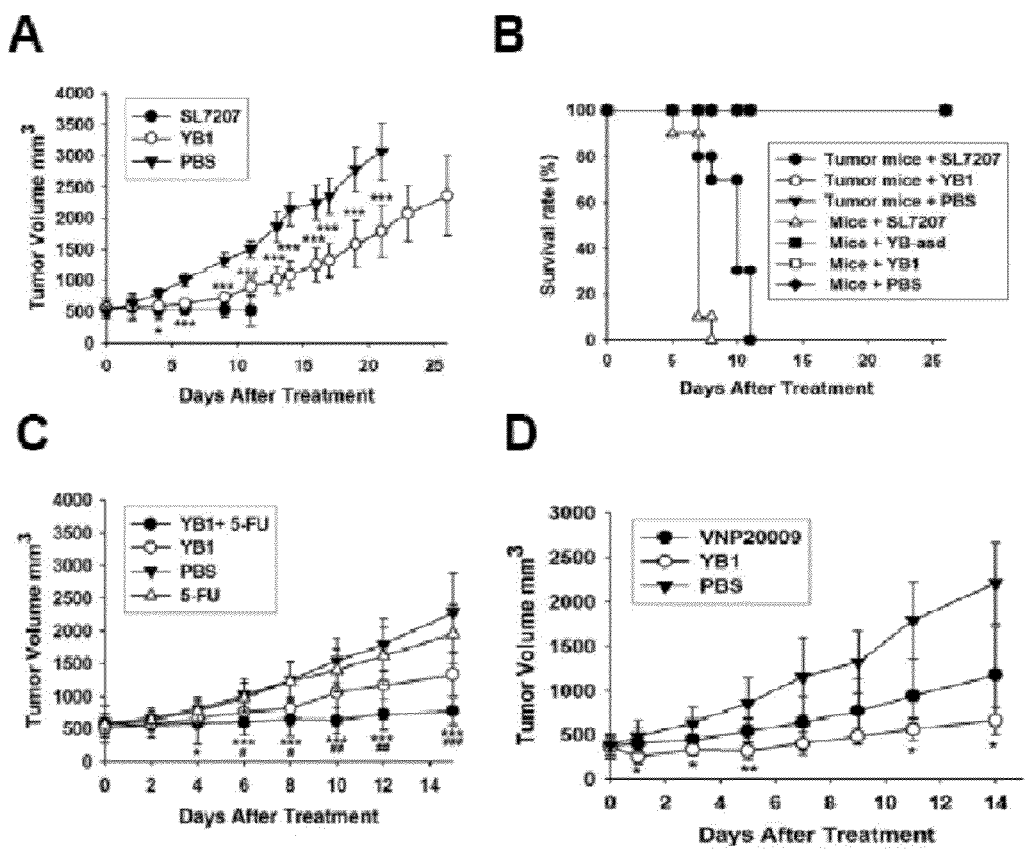

In one embodiment, described herein is the use of combination therapy with YB1 and chemotherapy. In one embodiment, the chemotherapy includes treatment with, but not limited to 5-FU which increase the tumor inhibition ability. 5-FU target rapidly dividing cells like cancer cells by blocking the action of thymidylate synthase [46]. When compared with untreated mice, YB1 considerably retarded tumor growth with an effectiveness greater than that of the drug 5-FU alone. In one embodiment, YB1 and 5-FU were more effective. SL7207 was too toxic and was lethal to the mice before effects on tumor growth could be observed (FIG. 13).

Described herein is an improved anticancer method than those utilize *Salmonella* strain VNP20009. VNP20009 was derived from strain YS72 [47], which was generated by nitrosoguanidine and UV irradiation induced random mutations from wild type *Salmonella typhimurium* 14028 [20]. This random mutagenesis strategy produces safe auxotrophic strains with compromised tumor targeting or killing abilities. VNP20009 in phase I clinical, in which inefficiency of tumor targeting and repressing was observed [48]. If some unknown functional genes of *Salmonella* were mutated in the process of attenuation, the VNP20009 might be over-attenuated [49]. On the contrary, strain SL7207 as the predecessor of YB1 was generated by aro transposon insertion [28]. The precise modification of *Salmonella* strain SL7207, by placing an essential gene under a hypoxia conditioned promoter, as performed in the present invention has successfully converted the bacterium to an "obligate" anaerobe, thereby removing the lethal toxicity of the host strain while maintaining its tumor targeting and enhancing its tumor killing abilities than VNP20009 (FIG. 9C & FIG. 13D). Furthermore, comparing with VNP20009, YB1 showed higher tumor habiting preference while the engineered YB1 strain also showed quicker eradication in normal organs (FIG. 9C). By resulting in less toxicity and better therapeutic performance, this novel strategy provides an alternative to conventional attenuation techniques, which may compromise bacterial tumor killing effect.

In one embodiment, described herein is a method to make the modified bacteria. Similar method may be used to make the modified bacteria of various strains. In one embodiment, the modified bacteria are Strain YB1 which is conditional obligate and facultative anaerobe. First, YB1 has specific tumor targeting ability as *C. sporogenes*, but it does not always need anaerobic condition for culture. Simple DAP supplement could restore YB1 as functional as normal facultative anaerobic bacteria. Second, YB1 as a strain of *Salmonella typhimurium* can share the same replication origin of plasmids with *E. coli*, it's easier and more convenient to construct plasmid-based drug delivery vector and to control the copy number of the vector in cancer therapy. While the ease of modifying *Chlostridia* to produce gene therapy vectors [17, 18] has improved [50], *Salmonella* can be readily transformed using long-established techniques and YB1 could be developed similarly. YB1-like bacteria have the advantages of an obligate anaerobic bacterium while maintaining the chemotaxic properties [5, 22] and ability to target metastasis [25-27] of *Salmonella*.

Conditioning *Salmonella* growth on hypoxia provides an alternative to conventional attenuation techniques, which require a mutation of the bacteria to compromise some normal function. The modified "obligate" anaerobe YB1 represents a new direction in producing bacterial therapeutic agents for cancer.

4. BRIEF DESCRIPTION OF THE FIGURES

The patent or application file contains at least one drawing executed in color. Copies of this patent or patent application publication with color drawing(s) will be provided by the Office upon request and payment of the necessary fee.

Figure 1B:
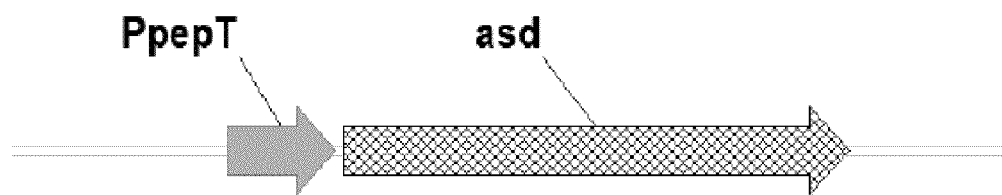
Figure 1C:
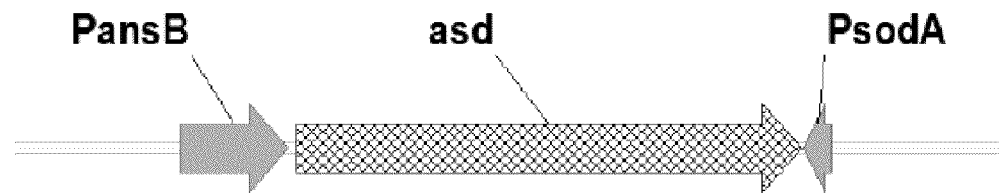

FIGS. 1A-C. (A) the construct (pYB1) of strictly hypoxia regulated an essential gene expressing cassette, which contained the sense promoter PpepT, asd gene, and the antisense promoter PsodA; (B) the construct (pYB-pw) without the antisense promoter PsodA; and (C) the construct (pYB-ew) with the different promoter PansB.

FIGS. 2A-D. (A) the DNA sequence of promoter PpepT (SEQ ID NO: 18); (B) the DNA sequence of asd gene (SEQ ID NO: 19); (C) the protein sequence of Asd protein (SEQ ID NO: 20); and (D) the DNA sequence of promoter PsodA (SEQ ID NO: 21).

Figure 3:
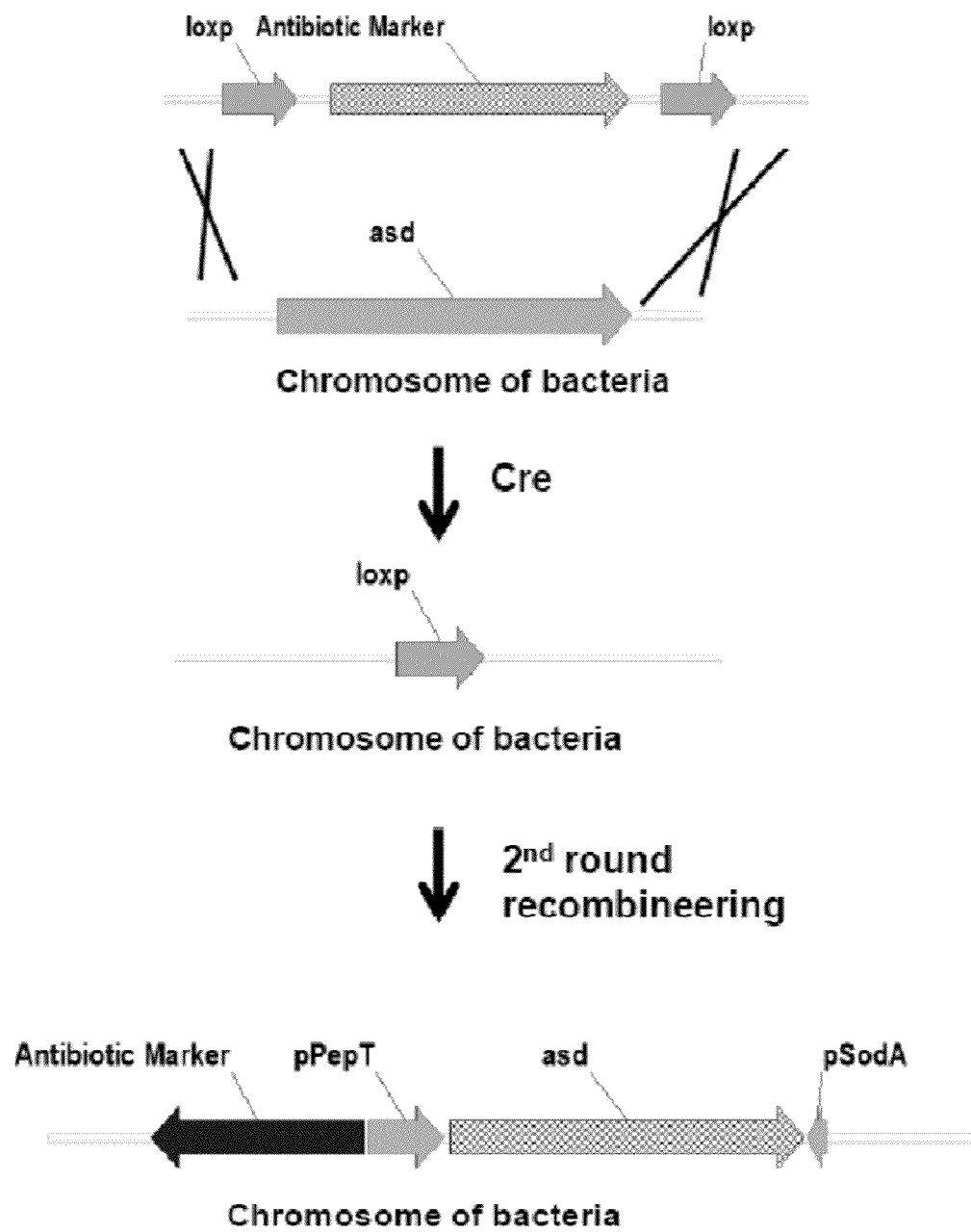

FIG. 3. The recombination engineering strategy replaces the original asd gene from the chromosome of bacteria with the strictly hypoxia regulated and chromosome-based an essential gene expressing cassette.

Figure 4B:
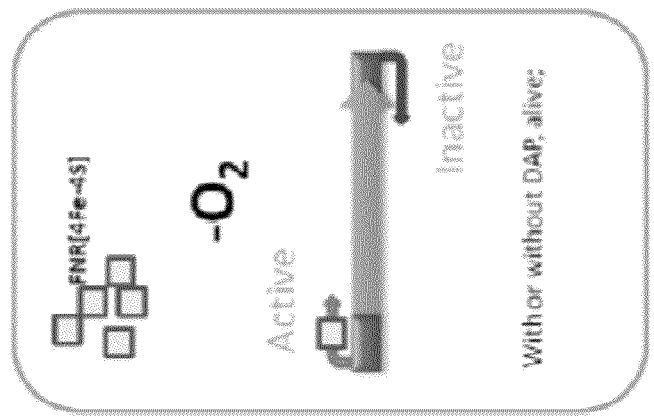
Figure 4A:
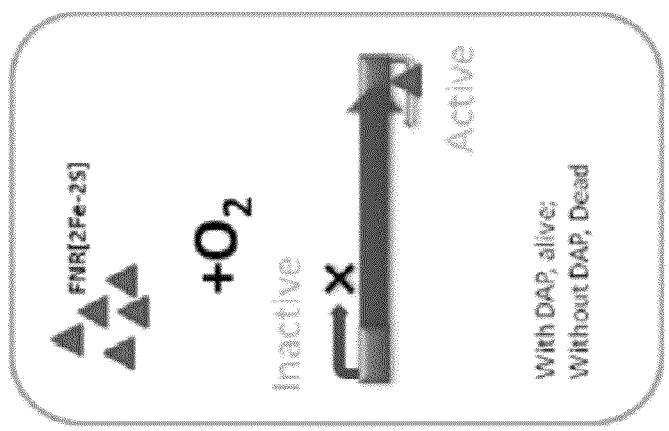

FIGS. 4A-B. The situation when YB1 is facing the environment with $O_2$ (A) and without $O_2$ (B).

FIGS. 5A-D. Growth rate of various strains ($10^4$ bacteria/ml) under aerobic or anaerobic conditions in LB broth without DAP (mean±sd, each time point represents three individual experiments). (C, D) as in (A, B) but with DAP.

FIG. 6. To test asd expression in response to oxygen, strains YB-myc-EW, YB-myc-PW, and YB1 were cultured under aerobic ($+O_2$) or anaerobic ($-O_2$) conditions for 24 hours at 37° C. DAP was added to prevent cell lysis under aerobic conditions. Bacterial cell number was quantified by $OD_{600}$ measurement and total protein was extracted from those bacteria respectively.

FIG. 7. Different mutant strains at serial dilutions under decreasing oxygen levels were cultured for 24 hours and bacterial growth was observed. Columns: 1 SL7207; 2 YB-asd; 3 YB1; 4 YB-pw; 5 YB-ew. (Three independent experiments were performed.)

Figure 8A:
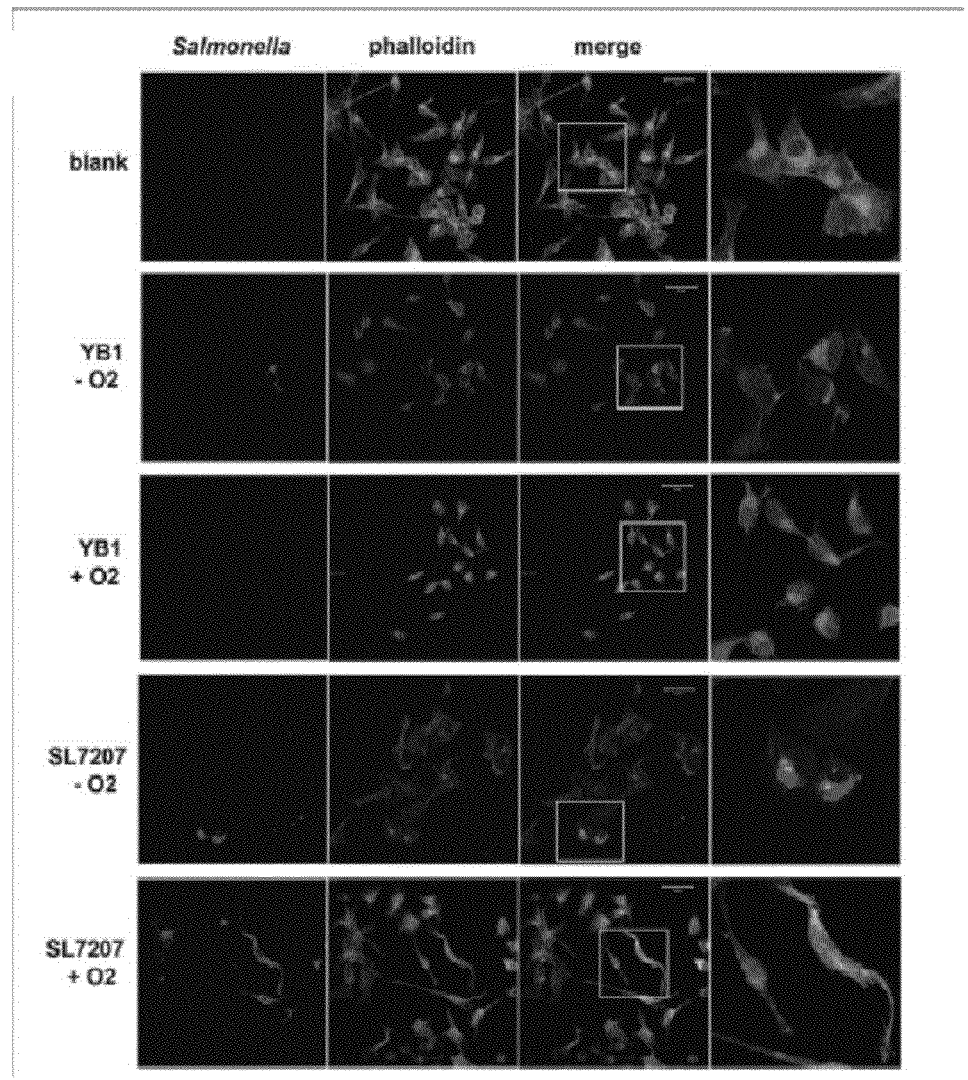
Figure 8B:
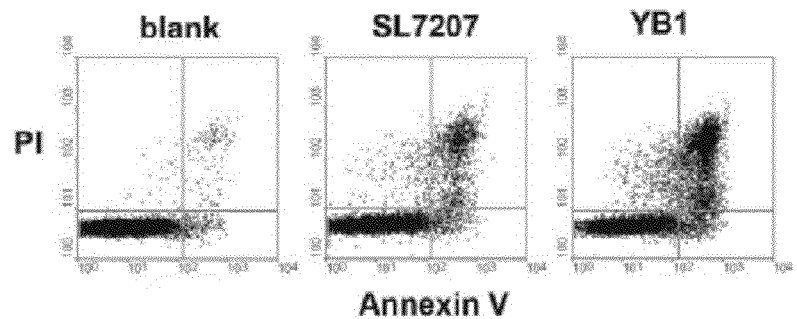
Figure 8C:
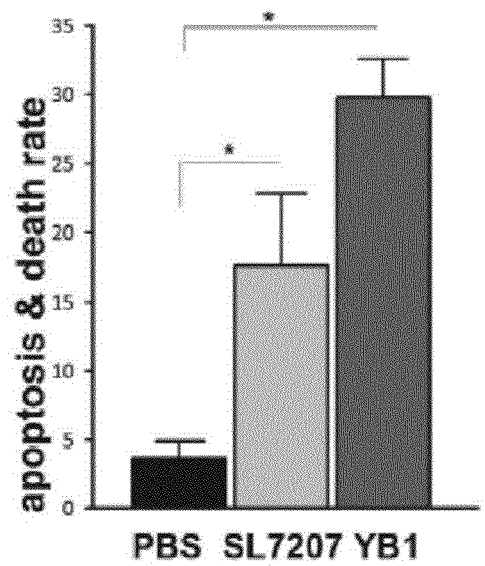

FIGS. 8A-C. YB1 and SL7207 in breast cancer cells (A) In vitro cultured breast cancer cells (MBA-MB-231) were exposed to YB1 and SL7207 (1: 500-1000) separately under anaerobic ($O_2$<0.5%: YB1–$O_2$, SL7207–$O_2$) or aerobic ($O_2$=21%; YB1+$O_2$, SL7207+$O_2$) conditions. Two hours post-incubation, breast cancer cells were washed and fresh medium containing gentamycin (50 µg/ml) was added to remove extracellular bacteria. 24~48 hours later, breast cancer cells were collected, stained using an anti-*Salmonella* antibody (red) and phalloidin to indicate cancer cells (green) and observed by confocal microscopy. Merged and enlarged images are given. (B, C) Apoptosis and death rate of cancer cells induced by *Salmonella* under anaerobic conditions were detected by annexin-V/PI staining and measured by flow cytometry. *, P<0.05.

Figure 9A:
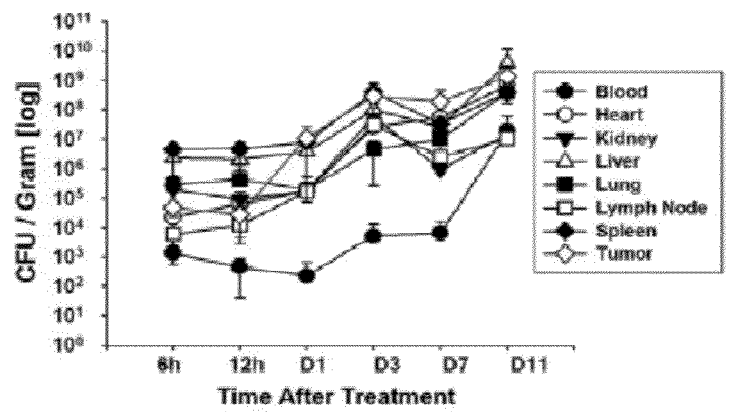
Figure 9B:
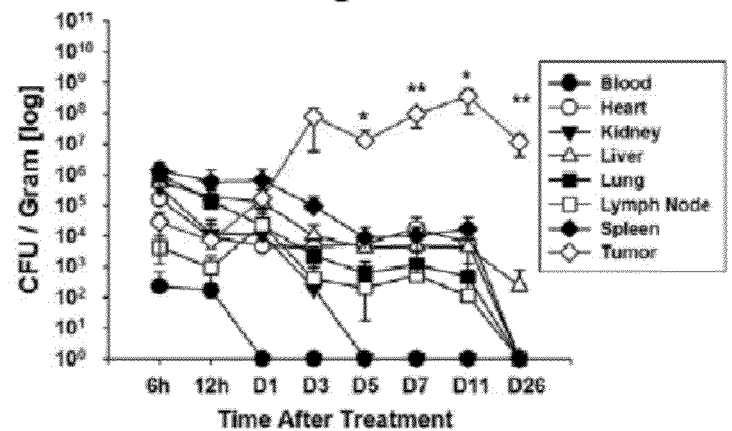
Figure 9C:
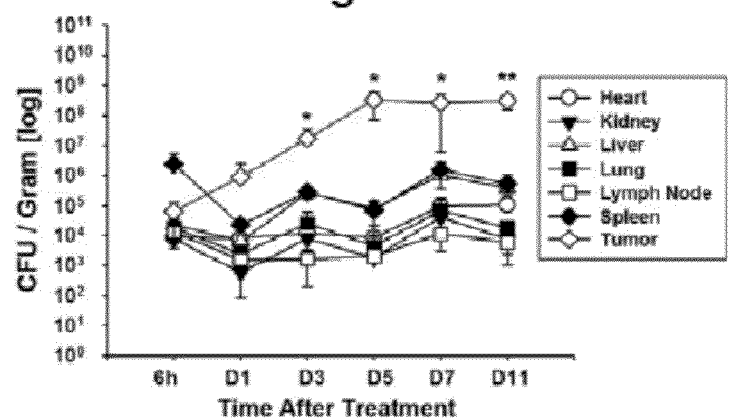

FIGS. 9A-C. CFU test of YB1, SL7207, and VNP20009 in breast tumor bearing nude mice. Nude mice with an MBA-MB-231 tumor received temporal vein injections of YB1, SL7207 or VNP20009. Mice were euthanized at the indicated time points and blood, heart, kidney, liver, lung, lymph node, spleen and tumor tissues were collected and homogenized and bacterial accumulation evaluated. In SL7207 (A) YB1 (B) or VNP20009 (C) treated mice, CFU counts per gram of most normal organs and tumor (red line) are shown over time (mean±sd, each time point represents three individual experiments with 2 mice for each experiment). *, tumor group vs. all other groups P<0.05; **P<0.01.

Figure 10:
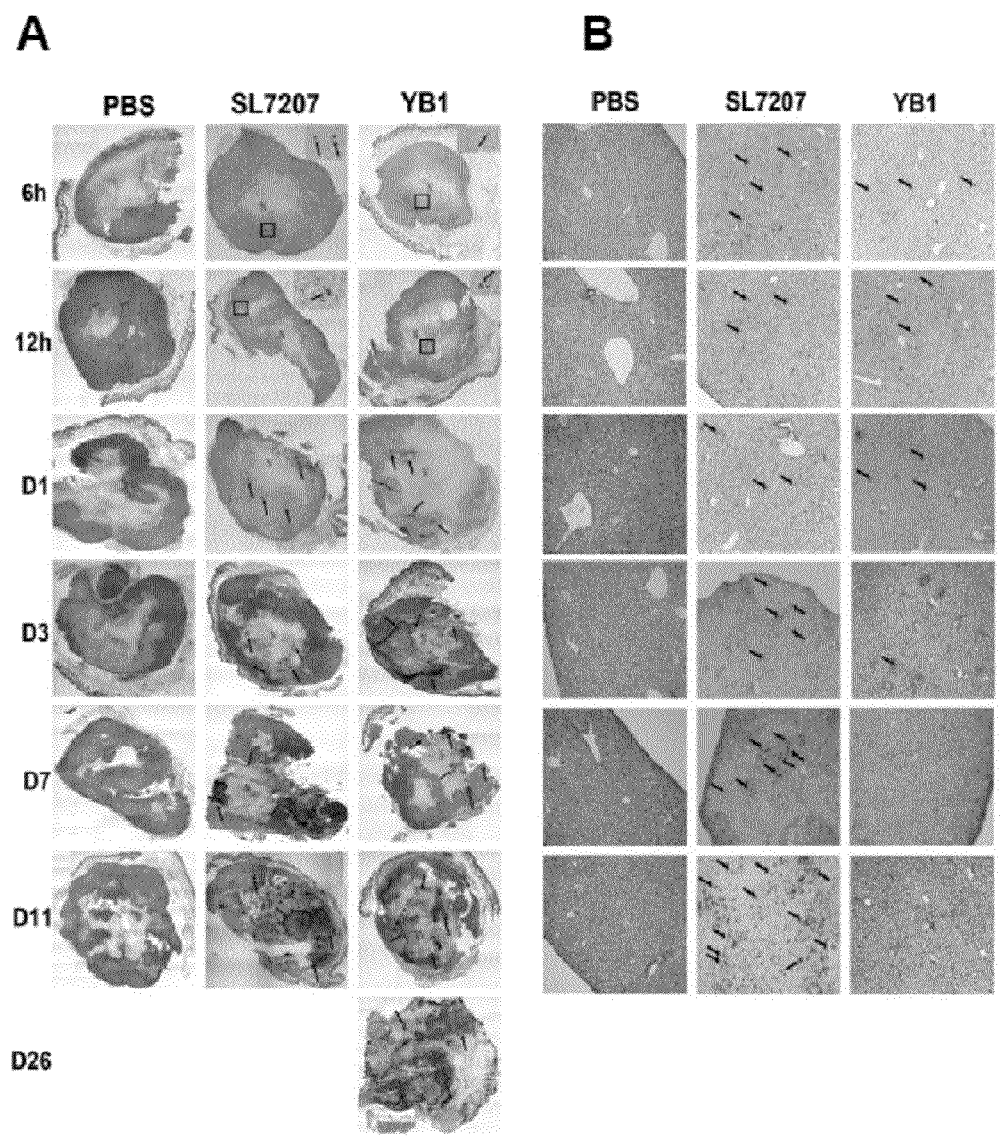

FIGS. 10 (A-B). Paraffin section test of YB1 and SL7207 in tumor and liver The distribution of *Salmonella* in tumor (A) and liver (B) of breast tumor bearing mice over time was demonstrated in tissue paraffin sections by immuno-staining, (Arrows: *Salmonella*).

Figure 11:
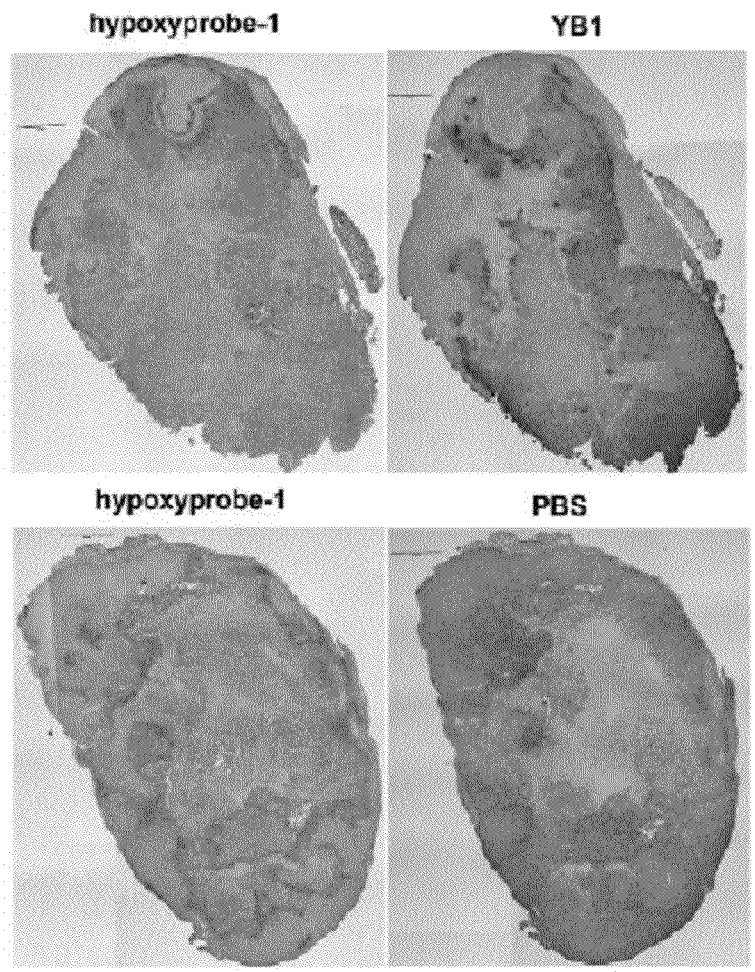

FIG. 11. YB1 colonization of the hypoxic region. YB1 and PBS treated tumor bearing mice were i.p. injected with hypoxyprobe-1 before being sacrificed. Tumor samples were removed, prepared and visualized with anti-*salmonella* or anti-hydroxyprobe-1 antibodies as noted in Materials and Methods. The transverse sections show an overview of the hypoxic area and YB1 distribution in the tumor. PBS treated tumor-bearing mice were used as a control.

Figure 12:
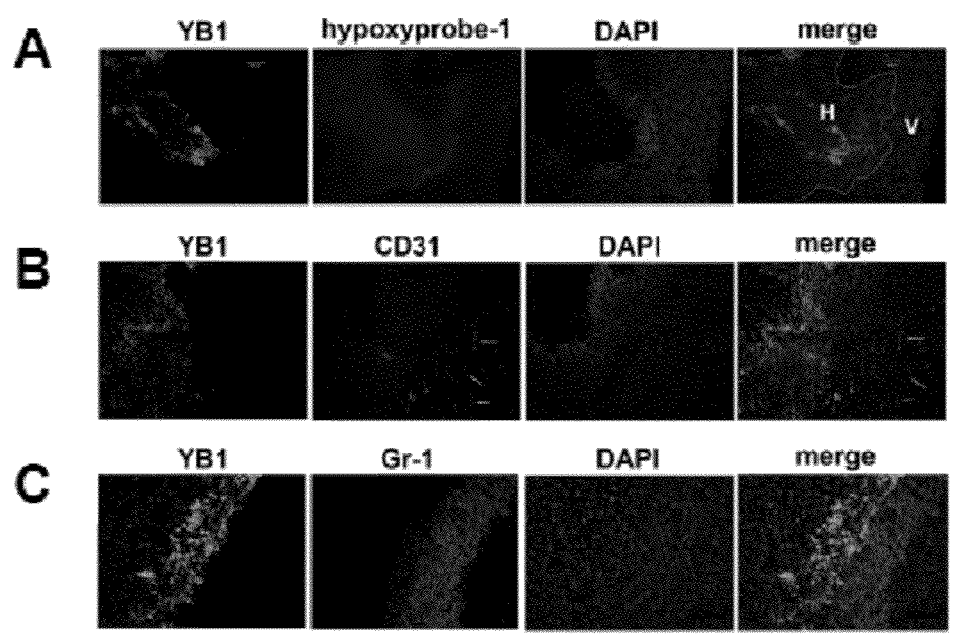

FIGS. 12 (A-C). Confinement of YB1 in the tumor. (A) YB1 and the hypoxic region are indicated by staining with anti-*Salmonella* (green) and anti-hypoxyprobe (red) antibodies, respectively. DNA is indicated by DAPI staining (purple). H: hypoxic area. V: viable area. (B) Blood vessels in the tumor are shown by an anti-CD31 antibody (red, arrows). (C) Immunocytes were detected with an anti-Gr-1 antibody (red).

FIGS. 13 (A-D). Repression of tumor growth by *Salmonella* strains. (A) Tumor volume (starting size about 500-550 $mm^3$) in mice injected with YB1, SL7207 or PBS (n=10, mean±sd). SL7207 treated mice died by day 11. *, YB1 group vs. PBS group, P<0.05; ***, P<0.001. (B) Survival chart for tumor free and tumor bearing mice treated with YB1, SL7207, YB-asd or PBS, respectively (n=10 each). (C) Tumor bearing mice were treated with YB1 or PBS (n=24 each). After three days, 5-FU was injected i.p. (60 mg/kg) to half the mice of each group (n=12) and repeated every three to four days for 2 weeks. *, YB1+5-FU group vs. PBS group and 5-FU group, P<0.05; ***, P<0.001; #, YB1+5-FU group vs. YB1 group, P<0.05; ##, P<0.01, ###, P<0.001. (D) Comparison of strain YB1 and VNP20009 for anti-tumor effect. Tumor volume (starting size about 360 $mm^3$) in mice after treatment with VNP20009, YB1, or PBS, respectively (n=6, mean±sd). *, YB1 group vs. VNP20009 group, P<0.05; **, P<0.01.

Figure 14A:
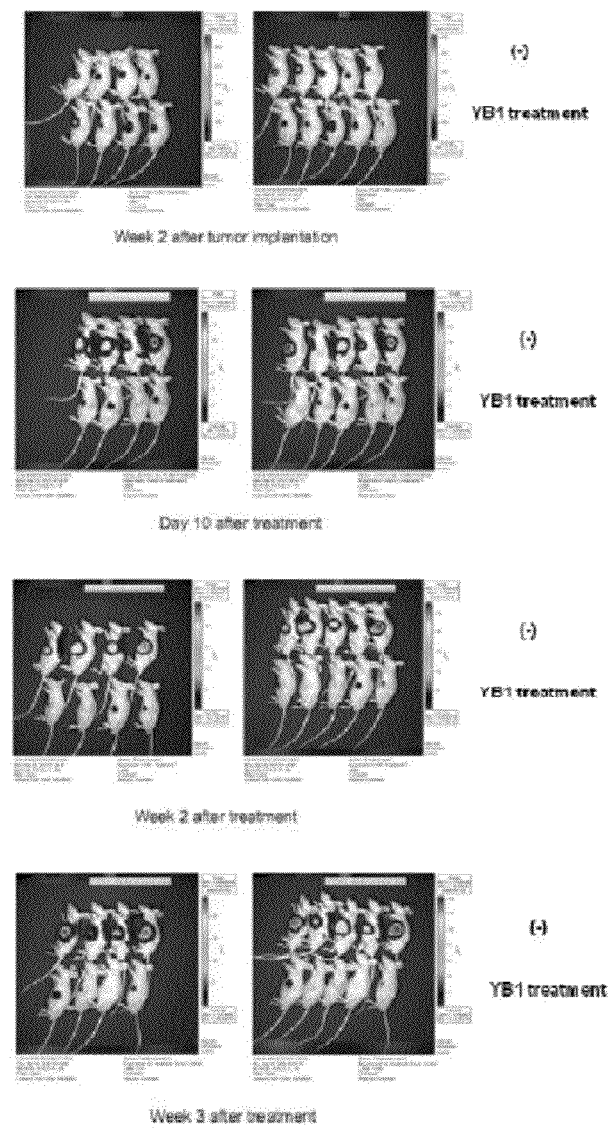

FIG. 14A. Monitoring in situ liver tumor growth with YB1 treatment. After two weeks of luciferase labeled MHCC97L tumor seeds were implanted into the left liver lobes of healthy nude mice group, 5E+07 CFU YB1 was i.v. administered though tail vein. The tumor growth was monitored by Xenogen IVIS 100 at different time points after YB1 treatment on day 0, day 10, week 2, and week 3. The upper panel is PBS treatment group. The lower panel is the YB1 treatment group. Each mouse was i.p. with 100 ug D-luciferin before imaging.

Figure 14B:
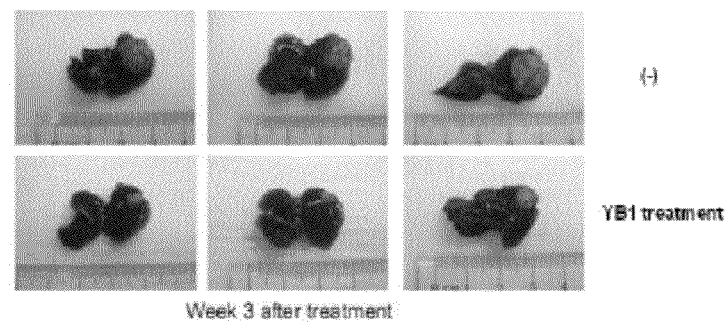
Figure 14C:
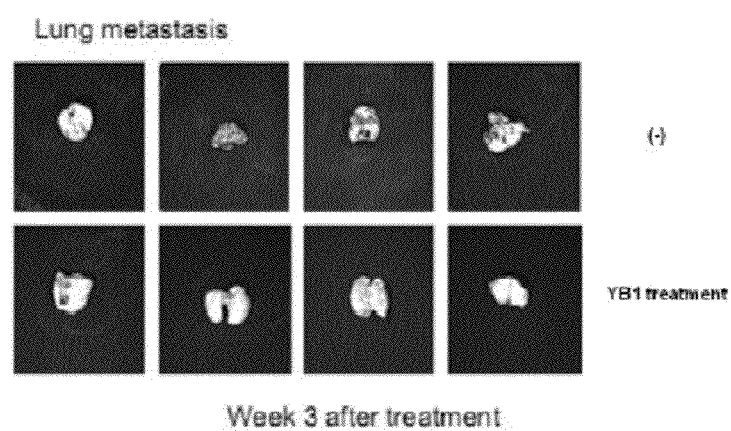

FIGS. 14B-C. Comparison of in situ tumor growth by histology and lung metastasis by live imaging with and without YB1 treatment in liver cancer nude mice model 3 weeks after tumor implantation. (B), comparison of tumor size in live tissues by histology; (C), examination of lung metastasis of MHCC97L tumor cells. The colorful signal indicated lung metastasis. The upper panel is PBS control group. The lower panel is YB1 treatment.

FIGS. 15A-C 'Window chamber' animal model. A, A nude mice for dorsal window chamber in the surgery; B, Window chamber model after surgery; C, Blood vessels distribution of window chamber under stereo microscopy.

FIGS. 16A-D 'Window Chamber' imaging for tumor progression under stereo microscopy. A, Transmission bright field imaging of blood vessels; B, Fluorescence imaging of tumor after three days implantation; C, D Enlarged image of blood vessels and tumor cells was found growth around vessels.

FIGS. 17A-D Observation the effect of YB1 treatment. A, Time-lapse track tumor regression caused by YB1 treatment from 30 mins to 5 days; B, In vivo image of alive cancer cells without YB1 treatment; C, D, Apoptosis of cancer cells induced by YB1 after 12 (C) and 36 hrs (D). signals are tdTomato labeled MDA-MB-231 cancer cells. Arrows indicate YB1 distributions. Scale bars, 100 μm.

FIGS. 18A-D Tumor infiltrating immune cells at different time points. A, tumor infiltrating immune cells; B, Ly6G+ neutrophils; C, CD19+ B lymphocytes; D, CD49b+ natural killer cells (NKs).

FIGS. 19A-F Paraffin-embedded biopsy of the distributions of YB1 and immune cells within tumor. A, B, C & D: paraffin tissue sections stained with anti-Ly6G antibody (shown as dark grey); Ly6G: a marker of neutrophils, E & F: tissue sections stained with anti-Salmonella antibody (shown as dark grey). Dash lines indicate tumor necrotic area.

Figure 20:
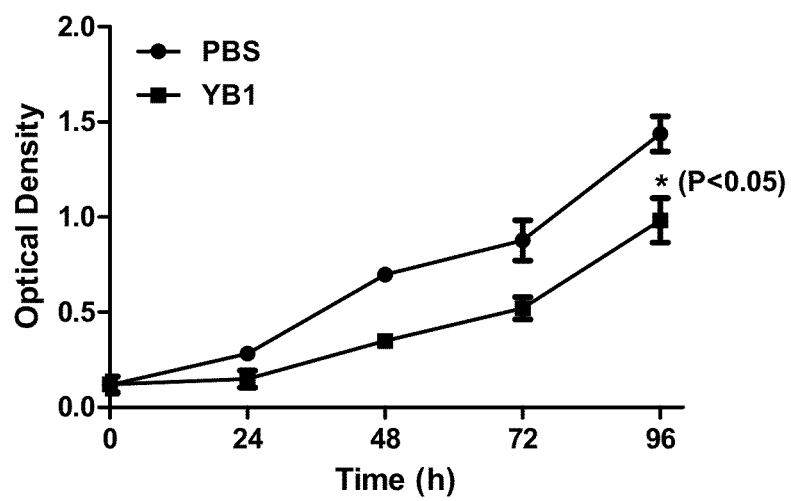

FIG. 20 Cell proliferation assay for Hela cells with or without YB1 treatment. Cells ($1 \times 10^3$) were seed in a 96 well plate and grew for overnight. After a 2 h-incubation of YB1 (M.O.I=1:200), cells were subsequently cultured for 24, 48, 72 and 96 hrs and MTT assay was performed. Absorbance was measured at 570 nm.

FIGS. 21A-E YB1 invasion assay with different cancer cell lines under anaerobic condition. Cancer cells of Lung cancer A549 (A), Colon cancer Caco-2 (B), Ovarian Cancer ov443 (C), Myeloma NS1 (D), and Neuroblastoma SH-SY5Y (E) were co-culture with YB1 (M.O.I=1:200) for 1 hr, washed by PBS for three times, and further cultured for 24 hrs under anaerobic condition. Signals are indicating intracellular YB1.

DETAILED DESCRIPTION

Since Salmonella is closely related to the Escherichia genus and has broad-host-range, its genomic information is clear and share many common features with E. coli. Comparing with gram-positive bacteria (e.g. Clostridium), Salmonella are easy for genetic manipulation, since it has thin membrane, sensitive to drug selection. It survives and proliferates within cells; therefore it can deliver genetic material (DNA, mRNA, microRNA etc.) into the cytoplasm with interrupt the nucleus. Most important, transfection with bacterial vector can avoid (random) genomic integration. Thus, it may directly deliver ectopic mRNA into host cells and utilize translation machinery of host cell to synthesize the corresponding exogenous proteins. On the other hand, since it is facultative anaerobic, it is easy to culture it in vitro and then send them to target hypoxic region within tumors. Thus, Salmonella can serve as both bacterial "weapon" and "vector" in research and medication. Moreover, attenuated Salmonella has been proved to be safe in human for years.

Anaerobic bacteria provide an important treatment opportunity in cancer therapy due to their ability to target the hypoxic region of solid tumors that is resistant to conventional treatment [1, 3]. If Salmonella, a facultative anaerobic bacteria, is to be a successful treatment agent in anti-cancer therapy, bacterial virulence in the host needs to be addressed [11]. In most cases attenuated forms are created and used as test therapeutic agents [24, 29, 34, 40]. However, the mutations required to attenuate a bacterium might also compromise its tumor targeting and killing ability. This was suggested as a possible reason for the poor performance of VNP20009 in clinical trials [11]. Recently, a systematic study of Salmonella mutants [41] partially addressed this issue by identifying several attenuated mutant bacteria with either mild or moderate reductions in tumor fitness. Tumor killing by these mutants could not be examined [41].

In one embodiment, described herein is a method in converting anaerobic bacteria into conditioned "obligate" anaerobe. In one aspect, the method is strictly hypoxia regulated and comprising transforming bacteria with an essential gene expressing cassette. In one aspect, the method comprises facultative anaerobic Gram-negative bacteria, including but not limited to S. typhimurium. In normal tissues under aerobic conditions, an essential gene asd is not expressed, diaminopimelic acid (DAP) is not synthesized and the bacteria will lyse during growth unless DAP is supplied by the environment. In tumor bearing nude mice, the modified bacteria inhibited tumor growth while not affecting the mice. In contrast, the original Salmonella strain was lethal to the mice.

Several attenuated Salmonella strains have been developed for tumor targeting studies. SL7207, which has a defect in the aroA gene and is a derivative of similar attenuated strains [28], has been used by several groups [29-33], although it can affect the health of immuno-compromised mice [29, 33]. Deletions in purI and msbB gave rise to VNP20009 [21, 34] which has been used for gene-targeted pro-drug therapy [35] and tested for oral delivery [36] and in clinical trials [37, 38]. Strain A1 [39] and its derivative A1-R [24] are leucine-arginine auxotrophs and A1-R targeted a metastases model [26]. Defects in guanosine 5'-diphosphate-3'-diphosphate synthesis attenuated Salmonella (strain ΔppGpp) [40] which has been shown to be effective as an inducible vector against CT-26 tumors and metastases [23]. The different nutritional environment in a tumor may compensate for the metabolic defects in these bacteria, thereby allowing effective growth in a tumor but not in normal tissues [20, 39].

However, attenuation to reduce virulence in normal tissues might compromise the function of the bacteria in tumors. A large-scale study used a transposon library and a custom microarray to identify a group of Salmonella mutants that had reduced fitness or attenuation in normal tissues [41]. Their aim was to identify attenuated strains that retain their fitness inside tumors. Two classes of attenuated strains, those with minor or with moderate reductions in tumor fitness, were identified. STM3120, a severely attenuated SPI-3 mutant, had a minor reduction in tumor fitness and was effective in PC-3 tumors and somewhat effective in oral administration [41]. An aroA mutant, similar to SL7207, had moderately reduced tumor fitness. However, this study examined bacterial fitness in tumors, not tumor killing ability.

In one embodiment, described herein is a modified bacteria comprising a strictly hypoxia regulated essential gene expressing cassette. By using recombinant technology, this cassette was introduced into the genome of facultative anaerobic gram-negative bacteria, including, but not limited to Salmonella typhimurium. A conditional "obligate" anaerobe strain YB1 is then produced. This strain YB1 was further applied to inhibit and reduce the growth of a solid tumor cancer when administered in vivo.

4.1 Method of Making a Hypoxia Targeted Salmonella Strain (YB1)

Replacement of the essential gene asd from parental Salmonella typhimurium strain SL7207 with a construct where this gene is under the control of hypoxia targeted promoters was achieved by recombinant technology (FIG. 3). In the resulting YB1 strain, the FNR related anaerobic capable promoter PpepT controls asd transcription while an aerobic promoter, P sodA, facilitates transcription of antisense asd that blocks any leakage of Asd expression under aerobic conditions (FIG. 1A). If asd is not transcribed and DAP is not supplied in the environment, lysis of the YB1 bacteria occur during bacterial growth.

Several other strain variants were constructed (YB-asd—SL7207 with no asd gene; YB1-pw—as YB1 but with no antisense promoter for asd; YB1-ew—as YB1 but with the PpepT promoter replaced with a weaker ansa promoter) (FIG. 1B, C). Regulation of Asd expression under high and low oxygen levels was tested. Changes in Asd protein levels were demonstrated by immunoblotting of myc tagged asd. The result (FIG. 6) showed that Asd expression in the YB1 (YB1-myc) strain was controlled by oxygen as expected: very strong Asd expression was detected under anaerobic condition whilst no such expression was observed under aerobic condition (YB1+$O_2$ and YB1-$O_2$). However, no Asd expressions were observed under either aerobic or anaerobic conditions (EW+$O_2$ and EW-$O_2$) in strain YB1-ew (YB-myc-ew) with the weak PansB promoter. In YB1-pw (YB-myc-pw) strain without antisense promoter, leaky Asd expression was observed under aerobic conditions (PW+$O_2$ and PW-$O_2$).

All of the mutants were tested for growth in LB broth (FIG. 5A-D). Of the engineered strains in the absence of DAP, only YB1 showed the combination of growth under anaerobic culture conditions and repression in the aerobic environment. SL7207 and YB-pw showed growth in all conditions. YB-asd and YB-ew showed growth only with addition of DAP.

Serial reductions in the oxygen level and bacterial concentration were used to establish the range of conditions under which YB1 and the other strains could survive in the presence or absence of DAP. On LB agar plates without DAP, YB1 grew only when oxygen levels decreased to below 0.5%. Strains YB-asd and YB-ew did not grow in the absence of DAP, while SL7207 and YB-pw grew in all conditions (FIG. 7).

4.2 Ability of YB1 to Invade Cancer Cells

Breast cancer cell line MDA-MB-231 samples were incubated with YB1 or SL7207 under oxygen concentrations below 0.5% or aerobic conditions. After removal of extracellular bacteria and further culturing, confocal microscopy showed that both SL7207 and YB1 had invaded the breast cancer cells under anaerobic conditions (FIG. 8A, YB1-$O_2$, SL7207-$O_2$). In comparison, under aerobic conditions (FIG. 8A, YB1+$O_2$, SL7207+$O_2$), YB1 could not survive and only SL7207 was observed in breast cancer cells. In anaerobic conditions, by using an annexin V/PI assay, MDA-MB-231 samples treated with each of the bacteria showed an increase in the number of dying or apoptotic cells relative to a blank control (FIG. 8B), with YB1 being somewhat more effective in causing cell death or apoptosis (P<0.05) (FIG. 8C).

4.3 Accumulation of SL7207, YB1, and VNP20009 in Tumor and Normal Tissues In Vivo Three groups of four-week-old nude mice were inoculated with breast cancer cells and, when tumor volumes reached 500-550 mm$^3$, a single dose of SL7207 or YB1 or VNP20009 was injected via the tail vein. At varying time points, mice were euthanized and most organs and tumor were collected, homogenized and cultured on LB agar plates with antibiotics and DAP. CFU/gram was used as a relative measure of the degree of colonization of the tissues with bacteria.

For SL7207 inoculated mice, 1E+02 to 1E+04 CFU/gram of bacteria were found in all tissues at 6 hours (FIG. 9A), except for the level in blood which was much higher (1.3E+03 CFU/gram). Bacterial levels increased in all tissues subsequently with an uncontrolled infection by day 3 (FIG. 9A). The tumor to liver ratio of SL7207 was 2.78:1 at day 3. Mice started to die on day 7. On day 11, SL7207 levels in liver reached 3.8E+09 CFU/gram (FIG. 9A) and after that all mice died.

For YB1 injected mice, levels of bacteria were approximately the same as for the SL7207 inoculated mice in all tissues 6 hours after inoculation (FIG. 9B), and bacteria were eliminated in the blood of 70% of the mice. After 1 day YB1 was eliminated from the blood and subsequently the levels in all normal tissues rapidly declined. In tumor, YB1 levels increased to a plateau of ~1E+08 CFU/gram by day 3 (FIG. 9B) The tumor to liver ratio of YB1 CFU/gram was ~7,000:1 on day 3 and ~20,000:1 on day 7 (FIG. 9B). By day 26, YB1 was totally eliminated from heart, kidney, lung, lymph node, and spleen. YB1 was also eliminated from liver in five of the six mice tested, remaining in one mouse with a CFU/gram of 1.3E+03. YB1 showed significant preference in tumor than other organs (P<0.05 on day 5 and day 11; P<0.01 on day 7 and day 26). No YB1 was detected inside bone marrow within the whole process of the experiments.

The accumulation of VNP20009 in different organs was also evaluated by CFU test. Like YB1, VNP20009 also showed tumor preference (P<0.05) as previous reported [21, 47]. The distribution in tumor reached to a plateau of ~3E+08 CFU/gram by day 5 (FIG. 9C). The best tumor to liver ratio was ~3,900:1 on day 5 (FIG. 9C). Compared with the SL7207 strain, VNP20009 demonstrated quick clearance in normal organs, but at a slower elimination speed than YB1 in liver (P<0.05), kidney (P<0.05), spleen (P<0.05), lung, lymph node, and heart (FIG. 9).

Immuno-staining of sections of tumor and liver confirmed the distribution of Salmonella bacteria in these tissues. Both YB1 and SL7207 targeted the tumor, with large amounts of bacteria being present from day 3 onwards (FIG. 10A). In liver, YB1 decreased and was almost eradicated by day 7 with little effect on liver structure (FIG. 10B). For SL7207 treated mice, continuing bacterial accumulation and liver damage were obvious (FIG. 10B).

4.4 YB1 Targeting of Hypoxic and Necrotic Regions in Tumors

Hypoxyprobe™-1 (pimonidazole hydrochloride) was used as a hypoxia marker to demonstrate the distribution of Salmonella in tumors. When immunostaining breast cancer tumor sections, hypoxic and necrotic areas were found (FIG.

11), which is consistent with previous reports. After the injection of *Salmonella* into tumor-bearing mice, most bacteria accumulated in the Hypoxyprobe™-1 marked region (FIG. 12A). Formation of hypoxic regions in a tumor might be due to disorganization of blood vessel development. The area colonized by YB1 had little or no blood vessels as indicated by CD31 staining (FIG. 12B), which suggested colonization by bacteria of the hypoxic region in the tumor. Staining with a GR-1 antibody to examine the immune response to bacterial invasion revealed infiltration of Gr-1+ host neutrophils into the breast tumor where they appeared to form a barrier around YB1 (FIG. 12C).

4.5 YB1 Inhibited Tumor Growth In Vivo

As YB1 invaded MDA-MB-231 breast cancer cells in vitro, causing cell apoptosis, its effect in vivo was measured. Tumor growth (tumor volume at bacterial inoculation ~500-550 mm$^3$) in YB1 treated mice was initially inhibited and then delayed relative to PBS treated mice (P<0.05 on day 3, P<0.001 from day 5 to day 21) (FIG. 13A). Little further tumor growth was seen in SL7207 treated mice as bacterial toxicity caused death between days 7 and 11 (FIG. 13A). Mice treated with YB1 (with or without a tumor) and YB-asd treated tumor free mice survived more than 25 days as did mice (with or without a tumor) treated with PBS (FIG. 13B). SL7207 treated mice started to die on days 5 and 7 with all mice dying by days 8 and 11 (without or with a tumor, respectively). SL7207 treated mice with a tumor had a slightly better survival rate (FIG. 13B).

While the reduction in tumor growth in YB1 treated mice was marked compared with PBS treated mice, the tumor was still growing. Treatment of tumor bearing mice with the therapeutic agent 5-FU showed only a small reduction in tumor growth relative to PBS treatment (P>0.05). However, when 5-FU was given to YB1 infected tumor bearing mice, a much greater reduction in tumor size was observed than with the individual treatments (YB1+5-FU group vs. PBS group or 5-FU group showed P<0.05 on day 4 and P<0.001 from day 6 to day 15; YB1+5-FU group vs. YB1 group showed P<0.05 on day 6, 8, P<0.01 on day 10, 12, and P<0.001 on day 15) (FIG. 13C).

4.6 Comparison of Strain YB1 and VNP20009 in Tumor Regression and Targeting

To further evaluate the anti-tumor effect of YB1 strain, we compared it with the well-known tumor targeting strain VNP20009. A single dose of VNP20009 or YB1 was also injected via the tail vein to breast tumor bearing mice (tumor volume at bacterial inoculation ~360 mm$^3$). The tumor size was measured every two days. Both YB1 (P<0.01) and VNP20009 (P<0.05) could delay tumor growth compared with PBS treatment group. However, YB1 showed stronger tumor inhibition than VNP20009 (P<0.05) (FIG. 13D).

4.7 YB1 Treatment of Liver Cancer in Nude Mice Model

In MHCC97-L liver cancer model, a single dose of YB1 treatment showed significant repression of liver cancer growth and metastasis (FIG. 14). The tumor growth was compared between the groups with YB1 treatment and PBS treatment, which was monitored by Xenogen IVIS imaging system (FIG. 14A). Distant lung metastasis was confirmed after histology examination (FIG. 14C). The imaging results showed the tumor was starting to shrink in size after 10 days' YB1 treatment. After 3 weeks, the tumor size of all treatment mice showed dramatically reduction. Some mice even showed totally elimination of tumors (FIG. 14).

5. EXAMPLES

5.1 Cloning and Assembling Strictly Hypoxia Regulated an Essential Gene Expressing Cassette Bacteria and plasmids used or created here are given in Table 1 and primers used are in Table 2. The asd gene and the promoter of the pepT gene were cloned from the chromosome of SL7207 by PCR with primer pairs asd-C-F and asd-C-R, pepT-F and pepT-R (preheating at 95° C. for 5 mins, followed by 30 cycles of denaturing at 95° C. for 30 seconds, annealing at 60° C. for 30 seconds, elongation at 72° C. for 1 min, with final extension at 72° C. for 10 minutes, and then cooling to room temperature) whilst asd-myc was generated with the asd-C-F and asd-C-myc-R primer pair. PansB and PsodA (promoters of ansB and sodA) constructs were generated by an annealing process with oligonucleotide pairs ansB-F and ansB-R, sodA-F and sodA-R (10 μM forward and reverse primers were mixed and heated at 95° C. for 5 mins, and placed at room temperature for 30 mins). The antibiotic marker was amplified by PCR with primers cm-F and cm-R from a ploxp-cm-loxp template [51]. The plasmids for the asd expression vectors were built on the backbone of pBluescript II SK (pBSK) which was digested by HindIII, XhoI, NotI and PstI. After ligation by T4 ligase, plasmids pYB1 (pBSK-cm-PpepT-asd-PsodA), pYB1-myc (pBSK-cm-PpepT-asd-myc-PsodA), pYB-pw (pBSK-cm-PpepT-asd), pYB-myc-pw (pBSK-cm-PpepT-asd-myc), pYB-ew (pBSK-cm-PansB-asd-PsodA), and pYB-myc-ew (pBSK-cm-PansB-asd-myc-PsodA) were generated.

TABLE 1

| | Relevant genotype or characteristics | Ref. or source |
|---|---|---|
| Strain | | |
| *S. typhimurium* | | |
| SL7207 | hisG46 DEL407 [aroA::Tn10 {Tc$^s$}]; wild type in this study | [1] |
| VNP20009 | YS72; ΔpurI, ΔmsbB | ATCC |
| YB1 | SL7207; Cm$^R$; Δasd::cm-PpepT-asd-sodA | This patent |
| YB1-myc | SL7207; Cm$^R$; Δasd::cm-PpepT-asd-myc-sodA | This patent |
| YB-asd | SL7207; Cm$^R$; Δasd | This patent |
| YB-pw | SL7207; Cm$^R$; Δasd::cm-PpepT-asd | This patent |
| YB-myc-pw | SL7207; Cm$^R$; Δasd::cm-PpepT-asd-myc | This patent |
| YB-ew | SL7207; Cm$^R$; Δasd::cm-PansB-asd-sodA | This patent |
| YB-myc-ew | SL7207; Cm$^R$; Δasd::cm-PansB-asd-myc-sodA | This patent |
| Plasmid | | |
| pBluescript II SK | Ap$^R$; cloning vector | Stratagene |
| ploxp-cm-loxp | Ap$^R$, Cm$^R$; pBSK derivative containing loxp-cm-loxp fragment | [2, 3] |
| pSim6 | Ap$^R$; Lambda-red recombinase plasmid | [4] |
| p705Cre-Km | Km$^R$; cre-recombinase expressing plasmid | [2] |
| pYB1 | Ap$^R$, Cm$^R$; pBSK derivative with cm-PpepT-asd-sodA fusion | This patent |

TABLE 1-continued

| | Relevant genotype or characteristics | Ref. or source |
|---|---|---|
| pYB1-myc | Ap$^R$; Cm$^R$; pBSK derivative with cm-PpepT-asd-myc-sodA fusion | This patent |
| pYB-pw | Ap$^R$; Cm$^R$; pBSK derivative with cm-PpepT-asd fusion | This patent |
| pYB-myc-pw | Ap$^R$; Cm$^R$; pBSK derivative with cm-PpepT-asd-myc fusion | This patent |
| pYB-ew | Ap$^R$; Cm$^R$; pBSK derivative with cm-PansB-asd-sodA fusion | This patent |
| pYB-myc-ew | Ap$^R$; Cm$^R$; pBSK derivative with cm-PansB-asd-myc-sodA fusion | This patent |

[1] Hoiseth, S. K. & Stocker, B. A. Aromatic-dependent *Salmonella typhimurium* are non-virulent and effective as live vaccines. Nature 291, 238-239 (1981).
[2] Jin, Y., Watt, R. M., Danchin, A. & Huang, J. D. Small noncoding RNA GcvB is a novel regulator of acid resistance in *Escherichia coli*. BMC Genomics 10, 165 (2009).
[3] Yu, B. et al. A method to generate recombinant *Salmonella typhi* Ty21a strains expressing multiple heterologous genes using an improved recombineering strategy. Appl Microbiol Biotechnol. 91, 177-188 (2011).
[4] Datta, S., Costantino, N. & Court, D. L. A set of recombineering plasmids for gram-negative bacteria. Gene 379, 109-115 (2006).

TABLE 2

(SEQ ID NOS 1-17, respectively, in order of appearance)

| Primers | Sequence (5'-3') | Purpose |
|---|---|---|
| pepT-F | ATTTGCGGCCGCGTAAACGCAACGGATGGCTGACCGC | pepT promoter |
| pepT-R | CCCAAGCTTCTTTTCGTGACAACATTATTAATAAG | |
| asd-C-F | CCCAAGCTTTGGAGCGAAACCGATGAAAAATGTTGGTTTTAT CGGCTGGC | asd gene with or without myc-tag |
| asd-C-R | CCGCTCGAGCTACGCCAACTGGCGCAGCATTCGA | |
| asd-myc-C-R | CCGCTCGAGCTACAGATCTTCTTCGCTAATCAGTTTCTGTTC TTCCGCCAACTGGCGCAGCATTCGA | |
| ansB-F | ATTTGCGGCCGCTTTTTTGACCTGCCTCAAACTTTGTAGATC TCCAAAATATATTCACGTTGTAAATTG | ansB promoter |
| ansB-R | CCCAAGCTTCGCTACGCATTATCCCTTAGCTCTGTATGGGAA ATTTGACGTTAAACAATTTACAACGTGAATA | |
| sodA-F | GACGAAAAGTACGGCATTGATAATCATTTTCAATATCATTTA ATTAACTATAATGAACCAAC | sodA promoter |
| SodA-R | TCGAGTTGGTTCATTATAGTTAATTAAATGATATTGAAAATG ATTATCAATGCCGTACTTTTCGTCTGCA | |
| cm-F | ATTTGCGGCCGCCCGATCATATTCAATAACCCT | chloramphenicol resistance gene |
| cm-R | ATTTGCGGCCGCGACTAGTGAACCTCTTCGAGGG | |
| asd-F | GTATGGTGAAGGATGCGCCACAGGATACTGGCGCGCATACAC AGCACATCTCTTTGCAGGAAAAAACCGATCATATTCAATAAC CCT | knock-out asd gene from SL7207 chromosome |
| asd-R | ATGGCGGCGCTGACGCGCCTTATCCGGCCTACAGAACCACAC GCAGGCCCGATAAGCGCTGCAATAGCCGACTAGTGAACCTCT TCGAGGG | |
| YB1-F | GCTGGCGGCGGCAGTGCGCATCATTCAGGGTTCCGCGACCGT GGCGTGTTAGGGTTTTCCCAGTCACGACGTT | knock-in oxygen response cassette to SL7207 chromosome |
| YB1-R | TGCAATTAGCGCATTAATCACGTCTCTATCGATACGACTGGA CATGGTTTGAGCGGATAACAATTTCACACAGG | |
| YB1-test-F | GATTCTGGTCGCTTGTCTGG | Verification of insertion |
| YB1-test-R | ACATTCCAGTTTGCCGACTT | |

5.2 Construction of Oxygen Sensitive *Salmonella* Mutant (YB1)

The λ-Red recombination system (plasmid pSim6) [52] was used to replace the asd gene with the cm-PpepT-asd-sodA genetic circuit in SL7207. As a first step the target asd gene was generated with a ploxp-cm-loxp template in a PCR reaction, electroporated into recombination-competent cells and selected on chloramphenicol Luria-Bertani (LB) plates. Antibiotic resistance genes were removed by site-specific Cre/loxP mediated recombination by transformation of plasmid p705cre-Km, generating the strain YB-asd. Next, the cm-PpepT-asd-sodA genetic circuit was amplified from plasmid pYB1 and, after recombinant, the correct colony was selected and confirmed by PCR giving strain YB1. Strains YB1-his, YB-pw, and YB-ew were constructed similarly with the plasmids pYB1-myc, pYB-pw, pYB-pw-myc, pYB-ew, and pYB-ew as templates, respectively (FIG. 3).

5.3 YB1 in Different Environments

By controlling essential gene asd with inducible promoters, facultative anaerobic gram-negative bacteria were transferred into "obligate" anaerobe without otherwise interfering with the function of the bacterium. This novel kind "obligate" anaerobe is reversible. It has two phases: under anaerobic condition, it could grow and live as normal facultative anaerobic gram-negative bacteria; under aerobic condition, it has two choices. With additional chemical diaminopimelic acid (DAP), YB1 could act full functional as facultative anaerobic gram-negative bacteria, but without DAP, it could lyse and die in short period time. Therefore, oxygen and DAP are two important factors to control "obligate" anaerobic ability of YB1 (FIG. 4).

To test the growth of *Salmonella* strains and mutants under aerobic and anaerobic conditions, bacterial strains were grown in LB medium at 37° C., with shaking at 220 rpm over night. Aerobic conditions were achieved by shaking in broth, and anaerobic cultures were either grown in anaerobic tubes or an anaerobic jar (Mitsubishi Gas Chemical Company). Overnight cultures of *Salmonella* strains SL7207, YB-asd, YB1, YB-pw, and YB-ew were counted and diluted into samples at 5E+04 colony forming units (CFU)/ml, with each strain divided into two groups (with or without DAP) in LB broth, OD600 was measured every 30 minutes for aerobic cultures, and each hour for anaerobic cultures from 0 hours to 24 hours. For LB agar plate assays, an anaerobic jar was applied to generate different oxygen concentrations by combinations of AnaeroPacks and monitored by an oxygen meter. Ten serial dilutions of individual drops from a high concentration of 5E+06 CFU/ml to 5E+01 CFU/ml, where each drop contained 10 µl of bacterial culture, were added to plates that were cultured in an anaerobic jar at 37° C. for 2 days. The results were showed in FIGS. 5 & 7.

5.4 Bacteria Strains Invasion of Breast Cancer Cells in vitro

*Salmonella* and MDA-MB-231 cells were prepared and co-cultured at a ratio of 1000~500:1 for 2 hours under anaerobic (O2<0.5%) or aerobic conditions. The cells were then washed with PBS and cultured in gentamycin supplemented medium to remove extracellular bacteria. 24 hours later, cells were fixed in paraformaldehyde (4%) and stained with an anti-*Salmonella* antibody (1:500, Abeam) overnight at 4° C. A Cy3 conjugated secondary antibody was added and incubated for 1 hour at room temperature. Then FITC conjugated Phalloidin (1:1000) was applied to indicate cell boundaries. Images were observed under a confocal microscope. Cancer cell apoptosis and death induced by bacteria under anaerobic conditions were detected by an annexin V-PI kit (Biovision) according to manufacturer's instructions. As shown by flow cytometry, annexin V+/PI− cells are apoptotic and annexin V+/PI+ cells are dead. The results were showed in FIG. 8.

5.5 Bacteria Strains in the Treatment of Breast Cancer Nude Mice Model

5E+05 MDA-MB-231 cells were inoculated at the fat pad of four-week-old nude mice. The tumor volumes were calculated by the following formula: $4/3 \times \pi \times (h \times w^2)/8$, h=height and w=width. When the tumors grew to about 500-550 mm3 (15-19 days), mice were divided into groups for experiments. If tumors reached 4000 mm$^3$ (20 mm in diameter) [53], mice were euthanized.

To measure the effect of bacterial inoculation on mouse survival and tumor growth, two groups of 10 mice were treated with either YB1 (5E+07 CFU), SL7207 (5E+07 CFU), and 6 mice for PBS group with volume of 100 µl injected through the tail vein (i.v.). Tumor size (starting volume is about 500-550 mm$^3$) was measured by caliper every 2 to 3 days (FIG. 13 A). Mouse survival rate was recorded (FIG. 13 B). For VNP20009 and YB1 comparison test, additional 6 mice for each group were administrated with same dose (5E+07 CFU), but with smaller tumor starting size (about 360 mm$^3$) (FIG. 13 D).

To measure the bacterial distribution after inoculation, Mice were treated with same method as above and sacrificed at the indicated time points (a total of 6 mice of YB1 group and SL7207 group for each time point; 5 mice of VNP20009 group for each time point) and tissues were weighed, homogenized, serially diluted in PBS and plated with the required antibiotics and DAP. CFU were counted after two days growth. The experiments of YB1 and SL7207 treatment were repeated three times with two mice per time point per experiment; the experiments of VNP20009 treatment were repeated two times with 2-3 mice per time point per experiment (FIG. 9).

A possible synergistic effect of YB1 and 5-FU was tested in 48 tumor-bearing mice that were divided into four groups with 12 mice each and treated with PBS, PBS with 5-FU (60 mg/Kg), a single dose of YB1 (5E+07 CFU) or a single dose of YB1 (5E+07 CFU) plus 5-FU. For the 5-FU-treatment groups, 5-FU was intra-peritoneal (i.p) injected every four days starting from day 3 after bacterial injection (FIG. 13C).

5.6 YB1 in the Treatment of Liver Cancer Nude Mice Model

Male nude mice 4-6 weeks old were used. MHCC97L cells of 6E+05 were injected into the right flank subcutaneously of each mouse. Once the tumor reached to 0.8-1 cm in diameter, they were surgically removed and cut into cubes with 1-2 mm$^3$ in volume. Then the tumor seeds were implanted into the left liver lobes of another healthy nude mice group [54] for another 2 weeks. The dose of 5E+07 CFU of YB1 were applied to treat mice. The tumor growth was monitored by Xenogen IVIS 100 at different time points after YB1 treatment on day 0, day 10, week 2, and week 3. Each mouse was i.p. with 100 ug D-luciferin before imaging. The results were showed in FIG. 14.

5.7 Using Chronic Live Intravital Animal Imaging System ('Window Chamber') to Directly Observe the Anti-Tumor Effect of YB1

The dorsal skinfold window chamber is a sophisticated animal model, which could observe dynamic interaction of certain region with surrounding host tissue in mice. This chronic model offers a repeatable analysis of tumor progression, treatment, and angiogenesis during 2-3 weeks after tumor implantation [55, 56].

5.7.1 Construct 'Window Chamber' Animal Model

In the surgery, first, anesthetized mouse was placed it on a thermostatic blanket to maintain the body temperature. Second, the mouse was sterilized most skin of by 70% ethanol. Third, the dorsal skin was gently pulled loose, and attached with two pieces of window chamber clamps. Fourth, both sides of the skin were punched with three holes at the screw positions by 18 G needle. Fifth, the screws were inserted and fixed on the front window chamber though three holes (FIG. 15A). Sixth, the forward layer skin was hold by mosquito forceps and cut, and left the opposing layer intact. Seventh, about 20 ul tumor cells suspension were injected by 29 G syringe between the layer of fascial plane and dermis. Eighth, a glass coverslip was placed on the window and secured with retaining ring (FIGS. 15B, 15C). To avoid infection, each mouse was giving 500 mg streptomycin everyday by i.p. injection. This procedure was adapted from Palmer's protocol [56].

5.7.2 Observe Tumor Formation with 'Window Chamber' Model

After three days tumor implantation, mice were anaesthetized again and placed under stereo microscope (FIGS. 16A-

D). Tumor mass was found localized around blood vessels for supplying nutrient and oxygen. Magnified figured showed the details single tumor cells (FIG. 16D).

5.7.3 Observe the Anti-Tumor Effect of YB1 with 'Window Chamber' Model

When the tumor bearing mice model were ready, as showed in FIGS. 16A-D, 5E+07 CFU YB1 were i.v. injected though tail vein. 30 mins after treatment, YB1 was found localized within tumor region (FIG. 17A). After 12 hrs, tumor showed regression, and this effect lasted for 5 days until the whole area of tumor was eliminated (FIG. 17A). The apoptosis of cancer cells could be observed after 12 hrs and 36 hrs (FIGS. 17C, D).

5.8 Characterization of Immune Response in Tumor Microenvironment Interfered by YB1

After YB1 was administrated to tumor bearing mice, the innate immune system was activated (FIG. 12C). To investigate the details, tumors of different time points was dissected and dissolved into single cells, and were further analyzed by FACS (FIGS. 18A-D). The results indicated that after YB1 treatment, the total percentage of immune cells was increasing to two times compared with PBS control group on day 10 (FIG. 18A). Furthermore, most activated immune cells were neutrophils (FIGS. 18B, C, D). Paraffin section suggested YB1 were co-localized and surrounded with neutrophils (FIGS. 19A-F).

5.9. YB1 in the Treatment of Other Tumor Models In Vitro 5.9.1 Cell Proliferation Assay of Cervical Cancer Cell Line Hela 1E+03 Hela cells were seeded in a 96 well plate and grew overnight in incubator. After 2 h co-culture with YB1 (2E+05 CFU) supplied with DAP, cells were washed with PBS for three times and subsequently cultured for further 24, 48, 72 and 96 hrs. A MTT assay was performed to evaluate the anti-cancer effect of YB1 (FIG. 20).

5.9.2 YB1 Invasion Assay of Lung Cancer, Colon Cancer, Ovarian Cancer, Myeloma, and Neuroblastoma Under Anaerobic Condition Cancer cell lines of Lung cancer A549, Colon cancer Caco-2, Ovarian Cancer ov443, Myeloma NS1, and Neuroblastoma SH-SY5Y were seeded and cultured in 6 well plate respectively. 2E+07 CFU of YB1 were co-culture with different cancer lines for 24 hrs under anaerobic condition. The result indicated YB1 had a ability of invasion to all of these cell lines under anaerobic condition (FIGS. 21A-C).

5.9.3 Safety Test of YB1 in Rat Model

Fifteen Buffalo rats (about 200 g each) were divided into three groups (five rats for each group) to test the maximum tolerance dose of YB1. Each rat in high dose group was challenged with 5E+09 CFU (medium dose group with 5E+08 CFU; low dose group with 5E+07 CFU) though penis vein injection. All rats in high group were killed within one day after treatment. No death of Rats was observed in other groups for three weeks. Furthermore, there was no trace of YB1 within liver or spleen after three weeks' treatment. The result indicated YB1 was safe to administrate with 5E+08 CFU or lower by i.v. injection in Buffalo rat, which was 10 times higher than in mouse model.

6. HUMAN TREATMENT

6.1 Formulations

The modified bacteria provided herein can be administered to a patient in the conventional form of preparations, such as injections and suspensions. Suitable formulations can be prepared by methods commonly employed using conventional, organic or inorganic additives, such as an excipient selected from fillers or diluents, binders, disintegrants, lubricants, flavoring agents, preservatives, stabilizers, suspending agents, dispersing agents, surfactants, antioxidants or solubilizers.

Excipients that may be selected are known to those skilled in the art and include, but are not limited to fillers or diluents (e.g., sucrose, starch, mannitol, sorbitol, lactose, glucose, cellulose, talc, calcium phosphate or calcium carbonate and the like), a binder (e.g., cellulose, carboxymethylcellulose, methylcellulose, hydroxymethylcellulose, hydroxypropylmethylcellulose, polypropylpyrrolidone, polyvinylpyrrolidone, gelatin, gum arabic, polyethyleneglycol or starch and the like), a disintegrants (e.g., sodium starch glycolate, croscarmellose sodium and the like), a lubricant (e.g., magnesium stearate, light anhydrous silicic acid, talc or sodium lauryl sulfate and the like), a flavoring agent (e.g., citric acid, or menthol and the like), a preservative (e.g., sodium benzoate, sodium bisulfite, methylparaben or propylparaben and the like), a stabilizer (e.g., citric acid, sodium citrate or acetic acid and the like), a suspending agent (e.g., methylcellulose, polyvinyl pyrrolidone or aluminum stearate and the like) a dispersing agent (e.g., hydroxypropylmethylcellulose and the like), surfactants (e.g., sodium lauryl sulfate, polaxamer, polysorbates and the like), antioxidants (e.g., ethylene diamine tetraacetic acid (EDTA), butylated hydroxyl toluene (BHT) and the like) and solubilizers (e.g., polyethylene glycols, polyoxyl 15 hydroxystearate (branded/marketed as SOLUTOL®), lauroyl polyoxylglycerides (branded/marketed as GELUCIRE®) and the like). The effective amount of the modified bacteria provided herein in the pharmaceutical composition may be at a level that will exercise the desired effect.

In another embodiment, provided herein are compositions comprising an effective amount of modified bacteria provided herein and a pharmaceutically acceptable carrier or vehicle, wherein a pharmaceutically acceptable carrier or vehicle can comprise an excipient, diluent, or a mixture thereof. In one embodiment, the composition is a pharmaceutical composition.

Compositions can be formulated to contain a daily dose, or a convenient fraction of a daily dose, in a dosage unit. In general, the composition is prepared according to known methods in pharmaceutical chemistry. Capsules can be prepared by mixing the modified bacteria provided herein with a suitable carrier or diluent and filling the proper amount of the mixture in capsules.

6.2 Method of Use

Solid tumor cancers that can be treated by the methods provided herein include, but are not limited to, sarcomas, carcinomas, and lymphomas. In specific embodiments, cancers that can be treated in accordance with the methods described include, but are not limited to, cancer of the breast, liver, neuroblastoma, head, neck, eye, mouth, throat, esophagus, esophagus, chest, bone, lung, kidney, colon, rectum or other gastrointestinal tract organs, stomach, spleen, skeletal muscle, subcutaneous tissue, prostate, breast, ovaries, testicles or other reproductive organs, skin, thyroid, blood, lymph nodes, kidney, liver, pancreas, and brain or central nervous system.

In particular embodiments, the methods for treating cancer provided herein inhibit, reduce, diminish, arrest, or stabilize a tumor associated with the cancer. In other embodiments, the methods for treating cancer provided herein inhibit, reduce, diminish, arrest, or stabilize the blood flow, metabolism, or edema in a tumor associated with the cancer or one or more symptoms thereof. In specific embodiments, the methods for treating cancer provided herein cause the regression of a tumor, tumor blood flow, tumor metabolism, or peritumor edema, and/or one or more symptoms associated with the cancer. In other embodiments, the methods for treating cancer provided herein maintain the size of the tumor so that it does not increase, or so that it increases by less than the increase of a tumor after administration of a standard therapy as measured by conventional methods available to one of skill in the art, such as digital rectal exam, ultrasound (e.g., transrectal ultrasound), CT Scan, MRI, dynamic contrast-enhanced MRI, or PET Scan. In specific embodiments, the methods for treating cancer provided herein decrease tumor size. In certain embodiments, the methods for treating cancer provided herein reduce the formation of a tumor. In certain embodiments, the methods for treating cancer provided herein eradicate, remove, or control primary, regional and/or metastatic tumors associated with the cancer. In some embodiments, the methods for treating cancer provided herein decrease the number or size of metastases associated with the cancer.

In certain embodiments, the methods for treating cancer provided herein reduce the tumor size (e.g., volume or diameter) in a subject by at least about 5%, 10%, 15%, 20%, 25%, 30%, 35%, 40%, 45%, 50%, 55%, 60%, 65%, 80%, 85%, 90%, 95%, 99%, or 100%, relative to tumor size (e.g., volume or diameter) prior to administration of modified bacteria as assessed by methods well known in the art, e.g., CT Scan, MRI, DCE-MRI, or PET Scan. In particular embodiments, the methods for treating cancer provided herein reduce the tumor volume or tumor size (e.g., diameter) in a subject by an amount in the range of about 5% to 20%, 10% to 20%, 10% to 30%, 15% to 40%, 15% to 50%, 20% to 30%, 20% to 40%, 20% to 50%, 30% to 60%, 30% to 70%, 30% to 80%, 30% to 90%, 30% to 95%, 30% to 99%, 30% to 100%, or any range in between, relative to tumor size (e.g., diameter) in a subject prior to administration of modified bacteria as assessed by methods well known in the art, e.g., CT Scan, MRI, DCE-MRI, or PET Scan.

In certain embodiments, the methods for treating cancer provided herein reduce the tumor perfusion in a subject by at least about 5%, 10%, 15%, 20%, 25%, 30%, 35%, 40%, 45%, 50%, 55%, 60%, 65%, 80%, 85%, 90%, 95%, 99%, or 100%, relative to tumor perfusion prior to administration of modified bacteria as assessed by methods well known in the art, e.g., MRI, DCE-MRI, or PET Scan. In particular embodiments, the methods for treating cancer provided herein reduce the tumor perfusion in a subject by an amount in the range of about 5% to 20%, 10% to 20%, 10% to 30%, 15% to 40%, 15% to 50%, 20% to 30%, 20% to 40%, 20% to 50%, 30% to 60%, 30% to 70%, 30% to 80%, 30% to 90%, 30% to 95%, 30% to 99%, 30% to 100%, or any range in between, relative to tumor perfusion prior to administration of modified bacteria, as assessed by methods well known in the art, e.g., MRI, DCE-MRI, or PET Scan.

In particular aspects, the methods for treating cancer provided herein inhibit or decrease tumor metabolism in a subject as assessed by methods well known in the art, e.g., PET scanning. In specific embodiments, the methods for treating cancer provided herein inhibit or decrease tumor metabolism in a subject by at least about 5%, 10%, 15%, 20%, 25%, 30%, 35%, 40%, 45%, 50%, 55%, 60%, 65%, 80%, 85%, 90%, 95%, or 100%, relative to tumor metabolism prior to administration of modified bacteria, as assessed by methods well known in the art, e.g., PET scanning. In particular embodiments, the methods for treating cancer provided herein inhibit or decrease tumor metabolism in a subject in the range of about 5% to 20%, 10% to 20%, 10% to 30%, 15% to 40%, 15% to 50%, 20% to 30%, 20% to 40%, 20% to 50%, 30% to 60%, 30% to 70%, 30% to 80%, 30% to 90%, 30% to 95%, 30% to 99%, 30% to 100%, or any range in between, relative to tumor metabolism prior to administration of modified bacteria, as assessed by methods well known in the art, e.g., PET scan.

6.3 Patient Population

In some embodiments, a subject treated for cancer in accordance with the methods provided herein is a human who has or is diagnosed with cancer. In other embodiments, a subject treated for cancer in accordance with the methods provided herein is a human predisposed or susceptible to cancer. In some embodiments, a subject treated for cancer in accordance with the methods provided herein is a human at risk of developing cancer.

In one embodiment, a subject treated for cancer in accordance with the methods provided herein is a human infant. In another embodiment, a subject treated for cancer in accordance with the methods provided herein is a human toddler. In another embodiment, a subject treated for cancer in accordance with the methods provided herein is a human child. In another embodiment, a subject treated for cancer in accordance with the methods provided herein is a human adult. In another embodiment, a subject treated for cancer in accordance with the methods provided herein is a middle-aged human. In another embodiment, a subject treated for cancer in accordance with the methods provided herein is an elderly human.

In certain embodiments, a subject treated for cancer in accordance with the methods provided herein has a cancer that metastasized to other areas of the body, such as the bones, lung and liver. In certain embodiments, a subject treated for cancer in accordance with the methods provided herein is in remission from the cancer. In some embodiments, a subject treated for cancer in accordance with the methods provided herein that has a recurrence of the cancer. In certain embodiments, a subject treated in accordance with the methods provided herein is experiencing recurrence of one or more tumors associated with cancer.

In certain embodiments, a subject treated for cancer in accordance with the methods provided herein is a human that is about 1 to about 5 years old, about 5 to 10 years old, about 10 to about 18 years old, about 18 to about 30 years old, about 25 to about 35 years old, about 35 to about 45 years old, about 40 to about 55 years old, about 50 to about 65 years old, about 60 to about 75 years old, about 70 to about 85 years old, about 80 to about 90 years old, about 90 to about 95 years old or about 95 to about 100 years old, or any age in between. In a specific embodiment, a subject treated for cancer in accordance with the methods provided herein is a human that is 18 years old or older. In a particular embodiment, a subject treated for cancer in accordance with the methods provided herein is a human child that is between the age of 1 year old to 18 years old. In a certain embodiment, a subject treated for cancer in accordance with the methods provided herein is a human that is between the age of 12 years old and 18 years old. In a certain embodiment, the subject is a male human. In another embodiment, the subject is a female human. In one embodiment, the subject is a female human that is not pregnant or is not breastfeeding. In one embodiment, the subject is a female that is pregnant or will/might become pregnant, or is breast feeding.

In some embodiments, a subject treated for cancer in accordance with the methods provided herein is administered modified bacteria or a pharmaceutical composition thereof, or a combination therapy before any adverse effects or intolerance to therapies other than the modified bacteria develops. In some embodiments, a subject treated for cancer in accordance with the methods provided herein is a refractory patient. In a certain embodiment, a refractory patient is a patient refractory to a standard therapy (e.g., surgery, radiation, anti-androgen therapy and/or drug therapy such as chemotherapy). In certain embodiments, a patient with cancer is refractory to a therapy when the cancer has not significantly been eradicated and/or the one or more symptoms have not been significantly alleviated. The determination of whether a patient is refractory can be made either in vivo or in vitro by any method known in the art for assaying the effectiveness of a treatment of cancer, using art-accepted meanings of "refractory" in such a context. In various embodiments, a patient with cancer is refractory when one or more tumors associated with cancer, have not decreased or have increased. In various embodiments, a patient with cancer is refractory when one or more tumors metastasize and/or spread to another organ.

In some embodiments, a subject treated for cancer accordance with the methods provided herein is a human that has proven refractory to therapies other than treatment with modified bacteria, but is no longer on these therapies. In certain embodiments, a subject treated for cancer in accordance with the methods provided herein is a human already receiving one or more conventional anti-cancer therapies, such as surgery, drug therapy such as chemotherapy, anti-androgen therapy or radiation. Among these patients are refractory patients, patients who are too young for conventional therapies, and patients with recurring tumors despite treatment with existing therapies.

6.4 Dosage

In one aspect, a method for treating cancer presented herein involves the administration of a unit dosage of modified bacteria thereof. The dosage may be administered as often as determined effective (e.g., once, twice or three times per day, every other day, once or twice per week, biweekly or monthly). In certain embodiments, a method for treating cancer presented herein involves the administration to a subject in need thereof of a unit dose of modified bacteria that can be determined by one skilled in the art.

In some embodiments, a unit dose of modified bacteria or a pharmaceutical composition thereof is administered to a subject once per day, twice per day, three times per day; once, twice or three times every other day (i.e., on alternate days); once, twice or three times every two days; once, twice or three times every three days; once, twice or three times every four days; once, twice or three times every five days; once, twice, or three times once a week, biweekly or monthly, and the dosage may be administered orally.

6.5 Combination Therapy

Presented herein are combination therapies for the treatment of cancer which involve the administration of modified bacteria in combination with one or more additional therapies to a subject in need thereof. In a specific embodiment, presented herein are combination therapies for the treatment of cancer which involve the administration of an effective amount of modified bacteria in combination with an effective amount of another therapy to a subject in need thereof.

As used herein, the term "in combination," refers, in the context of the administration of modified bacteria, to the administration of modified bacteria prior to, concurrently with, or subsequent to the administration of one or more additional therapies (e.g., agents, surgery, or radiation) for use in treating cancer. The use of the term "in combination" does not restrict the order in which modified bacteria and one or more additional therapies are administered to a subject. In specific embodiments, the interval of time between the administration of modified bacteria and the administration of one or more additional therapies may be about 1-5 minutes, 1-30 minutes, 30 minutes to 60 minutes, 1 hour, 1-2 hours, 2-6 hours, 2-12 hours, 12-24 hours, 1-2 days, 2 days, 3 days, 4 days, 5 days, 6 days, 7 days, 1 week, 2 weeks, 3 weeks, 4 weeks, 5 weeks, 6 weeks, 7 weeks, 8 weeks, 9 weeks, 10 weeks, 15 weeks, 20 weeks, 26 weeks, 52 weeks, 11-15 weeks, 15-20 weeks, 20-30 weeks, 30-40 weeks, 40-50 weeks, 1 month, 2 months, 3 months, 4 months 5 months, 6 months, 7 months, 8 months, 9 months, 10 months, 11 months, 12 months, 1 year, 2 years, or any period of time in between. In certain embodiments, modified bacteria and one or more additional therapies are administered less than 1 day, 1 week, 2 weeks, 3 weeks, 4 weeks, one month, 2 months, 3 months, 6 months, 1 year, 2 years, or 5 years apart.

In some embodiments, the combination therapies provided herein involve administering modified bacteria daily, and administering one or more additional therapies once a week, once every 2 weeks, once every 3 weeks, once every 4 weeks, once every month, once every 2 months (e.g., approximately 8 weeks), once every 3 months (e.g., approximately 12 weeks), or once every 4 months (e.g., approximately 16 weeks). In certain embodiments, modified bacteria and one or more additional therapies are cyclically administered to a subject. Cycling therapy involves the administration of modified bacteria for a period of time, followed by the administration of one or more additional therapies for a period of time, and repeating this sequential administration. In certain embodiments, cycling therapy may also include a period of rest where modified bacteria or the additional therapy is not administered for a period of time (e.g., 2 days, 3 days, 4 days, 5 days, 6 days, 7 days, 1 week, 2 weeks, 3 weeks, 4 weeks, 5 weeks, 10 weeks, 20 weeks, 1 month, 2 months, 3 months, 4 months, 5 months, 6 months, 7 months, 8 months, 9 months, 10 months, 11 months, 12 months, 2 years, or 3 years). In an embodiment, the number of cycles administered is from 1 to 12 cycles, from 2 to 10 cycles, or from 2 to 8 cycles.

In some embodiments, the methods for treating cancer provided herein comprise administering modified bacteria as a single agent for a period of time prior to administering the modified bacteria in combination with an additional therapy. In certain embodiments, the methods for treating cancer provided herein comprise administering an additional therapy alone for a period of time prior to administering modified bacteria in combination with the additional therapy.

In some embodiments, the administration of modified bacteria and one or more additional therapies in accordance with the methods presented herein have an additive effect relative the administration of modified bacteria or said one or more additional therapies alone. In some embodiments, the administration of modified bacteria and one or more additional therapies in accordance with the methods presented herein have a synergistic effect relative to the administration of the Compound or said one or more additional therapies alone.

As used herein, the term "synergistic," refers to the effect of the administration of modified bacteria in combination with one or more additional therapies (e.g., agents), which combination is more effective than the additive effects of any two or more single therapies (e.g., agents). In a specific embodiment, a synergistic effect of a combination therapy permits the use of lower dosages (e.g., sub-optimal doses) of modified bacteria or an additional therapy and/or less frequent administration of modified bacteria or an additional therapy to a subject. In certain embodiments, the ability to utilize lower dosages of modified bacteria or of an additional therapy and/or to administer modified bacteria or said additional therapy less frequently reduces the toxicity associated with the administration of modified bacteria or of said additional therapy, respectively, to a subject without reducing the efficacy of modified bacteria or of said additional therapy, respectively, in the treatment of cancer. In some embodiments, a synergistic effect results in improved efficacy of modified bacteria and each of said additional therapies in treating cancer. In some embodiments, a synergistic effect of a combination of modified bacteria and one or more additional therapies avoids or reduces adverse or unwanted side effects associated with the use of any single therapy.

The combination of modified bacteria and one or more additional therapies can be administered to a subject in the same pharmaceutical composition. Alternatively, modified bacteria and one or more additional therapies can be administered concurrently to a subject in separate pharmaceutical compositions. Modified bacteria and one or more additional therapies can be administered sequentially to a subject in separate pharmaceutical compositions. Modified bacteria and one or more additional therapies may also be administered to a subject by the same or different routes of administration.

The combination therapies provided herein involve administering to a subject to in need thereof modified bacteria in combination with conventional, or known, therapies for treating cancer. Other therapies for cancer or a condition associated therewith are aimed at controlling or relieving one or more symptoms. Accordingly, in some embodiments, the combination therapies provided herein involve administering to a subject to in need thereof a pain reliever, or other therapies aimed at alleviating or controlling one or more symptoms associated with or a condition associated therewith.

Specific examples of anti-cancer agents that may be used in combination with modified bacteria include: a hormonal agent (e.g., aromatase inhibitor, selective estrogen receptor modulator (SERM), and estrogen receptor antagonist), chemotherapeutic agent (e.g., microtubule dissembly blocker, antimetabolite, topisomerase inhibitor, and DNA crosslinker or damaging agent), anti-angiogenic agent (e.g., VEGF antagonist, receptor antagonist, integrin antagonist, vascular targeting agent (VTA)/vascular disrupting agent (VDA)), radiation therapy, and conventional surgery.

Non-limiting examples of hormonal agents that may be used in combination with modified bacteria include aromatase inhibitors, SERMs, and estrogen receptor antagonists. Hormonal agents that are aromatase inhibitors may be steroidal or nonsteroidal. Non-limiting examples of nonsteroidal hormonal agents include letrozole, anastrozole, aminoglutethimide, fadrozole, and vorozole. Non-limiting examples of steroidal hormonal agents include aromasin (exemestane), formestane, and testolactone. Non-limiting examples of hormonal agents that are SERMs include tamoxifen (branded/marketed as Nolvadex®), afimoxifene, arzoxifene, bazedoxifene, clomifene, femarelle, lasofoxifene, ormeloxifene, raloxifene, and toremifene. Non-limiting examples of hormonal agents that are estrogen receptor antagonists include fulvestrant. Other hormonal agents include but are not limited to abiraterone and lonaprisan.

Non-limiting examples of chemotherapeutic agents that may be used in combination with modified bacteria include microtubule disassembly blocker, antimetabolite, topisomerase inhibitor, and DNA crosslinker or damaging agent.

Chemotherapeutic agents that are microtubule dissemby blockers include, but are not limited to, taxenes (e.g., paclitaxel (branded/marketed as TAXOL®), docetaxel, abraxane, larotaxel, ortataxel, and tesetaxel); epothilones (e.g., ixabepilone); and vinca alkaloids (e.g., vinorelbine, vinblastine, vindesine, and vincristine (branded/marketed as ONCOVIN®)).

Chemotherapeutic agents that are antimetabolites include, but are not limited to, folate anitmetabolites (e.g., methotrexate, aminopterin, pemetrexed, raltitrexed); purine antimetabolites (e.g., cladribine, clofarabine, fludarabine, mercaptopurine, pentostatin, thioguanine); pyrimidine antimetabolites (e.g., 5-fluorouracil, capcitabine, gemcitabine (GEMZAR®), cytarabine, decitabine, floxuridine, tegafur); and deoxyribonucleotide antimetabolites (e.g., hydroxyurea).

Chemotherapeutic agents that are topoisomerase inhibitors include, but are not limited to, class I (camptotheca) topoisomerase inhibitors (e.g., topotecan (branded/marketed as HYCAMTIN®) irinotecan, rubitecan, and belotecan); class II (podophyllum) topoisomerase inhibitors (e.g., etoposide or VP-16, and teniposide); anthracyclines (e.g., doxorubicin, epirubicin, Doxil, aclarubicin, amrubicin, daunorubicin, idarubicin, pirarubicin, valrubicin, and zorubicin); and anthracenediones (e.g., mitoxantrone, and pixantrone).

Chemotherapeutic agents that are DNA crosslinkers (or DNA damaging agents) include, but are not limited to, alkylating agents (e.g., cyclophosphamide, mechlorethamine, ifosfamide (branded/marketed as IFEX®), trofosfamide, chlorambucil, melphalan, prednimustine, bendamustine, uramustine, estramustine, carmustine (branded/marketed as BiCNUO), lomustine, semustine, fotemustine, nimustine, ranimustine, streptozocin, busulfan, mannosulfan, treosulfan, carboquone, N,N'N'-triethylenethiophosphoramide, triaziquone, triethylenemelamine); alkylating-like agents (e.g., carboplatin (branded/marketed as PARAPLATIN®), cisplatin, oxaliplatin, nedaplatin, triplatin tetranitrate, satraplatin, picoplatin); nonclassical DNA crosslinkers (e.g., procarbazine, dacarbazine, temozolomide (branded/marketed as TEMODAR®), altretamine, mitobronitol); and intercalating agents (e.g., actinomycin, bleomycin, mitomycin, and plicamycin).

Non-limiting examples of other therapies that may be administered to a subject in combination with a Compound include:

(1) a statin such as lovostatin (e.g., branded/marketed as MEVACOR®);
(2) an mTOR inhibitor such as sirolimus which is also known as Rapamycin (e.g., branded/marketed as RAPAMUNE®), temsirolimus (e.g., branded/marketed as TORISEL®), evorolimus (e.g., branded/marketed as AFINITOR®), and deforolimus;
(3) a farnesyltransferase inhibitor agent such as tipifarnib;
(4) an antifibrotic agent such as pirfenidone;
(5) a pegylated interferon such as PEG-interferon alfa-2b;
(6) a CNS stimulant such as methylphenidate (branded/marketed as RITALIN®);
(7) a HER-2 antagonist such as anti-HER-2 antibody (e.g., trastuzumab) and kinase inhibitor (e.g., lapatinib);
(8) an IGF-1 antagonist such as an anti-IGF-1 antibody (e.g., AVE1642 and IMC-A11) or an IGF-1 kinase inhibitor;
(9) EGFR/HER-1 antagonist such as an anti-EGFR antibody (e.g., cetuximab, panitumamab) or EGFR kinase inhibitor (e.g., erlotinib; gefitinib);
(10) SRC antagonist such as bosutinib;
(11) cyclin dependent kinase (CDK) inhibitor such as seliciclib;

(12) Janus kinase 2 inhibitor such as lestaurtinib;
(13) proteasome inhibitor such as bortezomib;
(14) phosphodiesterase inhibitor such as anagrelide;
(15) inosine monophosphate dehydrogenase inhibitor such as tiazofurine;
(16) lipoxygenase inhibitor such as masoprocol;
(17) endothelin antagonist;
(18) retinoid receptor antagonist such as tretinoin or alitretinoin;
(19) immune modulator such as lenalidomide, pomalidomide, or thalidomide;
(20) kinase (e.g., tyrosine kinase) inhibitor such as imatinib, dasatinib, erlotinib, nilotinib, gefitinib, sorafenib, sunitinib, lapatinib, or TG100801;
(21) non-steroidal anti-inflammatory agent such as celecoxib (branded/marketed as CELEBREX®);
(22) human granulocyte colony-stimulating factor (G-CSF) such as filgrastim (branded/marketed as NEUPOGEN®);
(23) folinic acid or leucovorin calcium;
(24) integrin antagonist such as an integrin α5β1-antagonist (e.g., JSM6427);
(25) nuclear factor kappa beta (NF-κβ) antagonist such as OT-551, which is also an anti-oxidant.
(26) hedgehog inhibitor such as CUR61414, cyclopamine, GDC-0449, and anti-hedgehog antibody;
(27) histone deacetylase (HDAC) inhibitor such as SAHA (also known as vorinostat (branded/marketed as ZOLINZA)), PCI-24781, SB939, CHR-3996, CRA-024781, ITF2357, JNJ-26481585, or PCI-24781;
(28) retinoid such as isotretinoin (e.g., branded/marketed as ACCUTANE®)
(29) hepatocyte growth factor/scatter factor (HGF/SF) antagonist such as HGF/SF monoclonal antibody (e.g., AMG 102);
(30) synthetic chemical such as antineoplaston;
(31) anti-diabetic, such as rosaiglitazone (e.g., branded/marketed as AVANDIA®)
(32) antimalarial and amebicidal drug such as chloroquine (e.g., branded/marketed as ARALEN®);
(33) synthetic bradykinin such as RMP-7;
(34) platelet-derived growth factor receptor inhibitor such as SU-101;
(35) receptor tyrosine kinase inhibitorsof Flk-1/KDR/ VEGFR2, FGFR1 and PDGFR beta such as SU5416 and SU6668;
(36) anti-inflammatory agent such as sulfasalazine (e.g., branded/marketed as AZULFIDINE™); and
(37) TOP-beta antisense therapy.

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All references cited herein are incorporated herein by reference in their entireties and for all purposes to the same extent as if each individual publication or patent or patent application was specifically and individually indicated to be incorporated by reference in its entirety for all purposes.

REFERENCES

| U.S. Pat. No. 7,514,089 | B2 | July 2009 Bermudes et al. |
| U.S. Pat. No. 7,354,592 | B2 | August 2008 Bermudes et al. |
| U.S. 2009/0208534 | A1 | August 2009 Xu et al. |
| U.S. 2010/0135973 | A1 | January 2010 Eisenstark et al. |
| U.S. Pat. No. 7,998,461 | B2 | August 2011 Forbes et al. |
| U.S. 2003/0175297 | A1 | September 2003 Urashima |
| U.S. 2006/0140975 | A1 | January 2006 Curtiss |

1. Brown, J. M. and W. R. Wilson, *Exploiting tumour hypoxia in cancer treatment*. Nat Rev Cancer, 2004. 4(6): p. 437-47.
2. Zhou, J., et al., *Tumor hypoxia and cancer progression*. Cancer Lett, 2006. 237(1): p. 10-21.
3. Pawelek, J., K. Low, and D. Bermudes, *Bacteria as tumour-targeting vectors*. Lancet Oncol, 2003. 4: p. 548-556.
4. St Jean, A. T., M. Zhang, and N. S. Forbes, *Bacterial therapies: completing the cancer treatment toolbox*. Curr Opin Biotechnol, 2008. 19(5): p. 511-7.
5. Kasinskas, R. W. and N. S. Forbes, *Salmonella typhimurium specifically chemotax and proliferate in heterogeneous tumor tissue in vitro*. Biotechnol Bioeng, 2006. 94(4): p. 710-21.
6. Wei, M. Q., et al., *Clostridial spores as live 'Trojan horse' vectors for cancer gene therapy: comparison with viral delivery systems*. Genet Vaccines Ther, 2008. 6: p. 8.
7. Kong, W., et al., *Regulated programmed lysis of recombinant Salmonella in host tissues to release protective antigens and confer biological containment*. PNAS, 2008. 105 (27): p. 9361-9366.
8. Wei, M. Q., et al., *Facultative or obligate anaerobic bacteria have the potential for multimodality therapy of solid tumours*. Eur J Cancer, 2007. 43(3): p. 490-6.
9. Dang, L. H., et al., *Combination bacteriolytic therapy for the treatment of experimental tumors*. Proc Natl Acad Sci USA, 2001. 98(26): p. 15155-15160.
10. Hall, S. S., *A commotion in the blood life, death, and the immune system*. 1st ed. 1997, New York: Henry Holt. xiv, 544 p. [8] p. of plates.
11. Leschner, S. and S. Weiss, *Salmonella-allies in the fight against cancer*. J Mol Med, 2010, 88(8): p. 763-73.
12. Sasaki, T., et al., *Genetically engineered Bifidobacterium longum for tumor-targeting enzyme prodrug therapy of autochthonous mammary tumors in rats*. Cancer Sci, 2006. 97(7): p. 649-57.
13. Yazawa, K., et al., *Bifidobacterium longum as a delivery system for cancer gene therapy: selective localization and growth in hypoxic tumors*. Cancer Gene Ther, 2000. 7(2): p. 269-74.
14. Yazawa, K., et al., *Bifidobacterium longum as a delivery system for gene therapy of chemically induced rat mammary tumors*. Breast Cancer Res Treat, 2001. 66(2): p. 165-70.
15. Barbe, S., L. Van Mellaert, and J. Anne, *The use of clostridial spores for cancer treatment*, J Appl Microbiol, 2006. 101(3): p. 571-8.
16. Van Mellaert, L., S. Barbe, and J. Anne, *Clostridium spores as anti-tumour agents*. Trends Microbiol, 2006. 14(4): p. 190-6.
17. Liu, S. C., et al., *Anticancer efficacy of systemically delivered anaerobic bacteria as gene therapy vectors targeting tumor hypoxia/necrosis*. Gene therapy, 2002. 9(4): p. 291-6.
18. Theys, J., et al., *Repeated cycles of Clostridium-directed enzyme prodrug therapy result in sustained antitumour effects in vivo*. British journal of cancer, 2006. 95(9): p. 1212-9.
19. Liu, S. C., et al., *Optimized clostridium-directed enzyme prodrug therapy improves the antitumor activity of the novel DNA cross-linking agent PR-104*. Cancer research, 2008. 68(19): p. 7995-8003.

20. Pawelek, J. M., K. B. Low, and D. Bermudes, *Tumor-targeted Salmonella as a novel anticancer vector.* Cancer Res, 1997. 57(20): p. 4537-44.
21. Low, K. B., et al., *Lipid A mutant Salmonella with suppressed virulence and TNFalpha induction retain tumor-targeting in vivo.* Nat Biotechnol, 1999. 17(1): p. 37-41.
22. Kasinskas, R. W. and N. S. Forbes, *Salmonella typhimurium lacking ribose chemoreceptors localize in tumor quiescence and induce apoptosis.* Cancer Res, 2007. 67(7): p. 3201-9.
23. Nguyen, V. H., et al., *Genetically engineered Salmonella typhimurium as an imageable therapeutic probe for cancer.* Cancer Res, 2010. 70(1): p. 18-23.
24. Zhao, M., et al., *Targeted therapy with a Salmonella typhimurium leucine-arginine auxotroph cures orthotopic human breast tumors in nude mice.* Cancer Res, 2006. 66(15): p. 7647-52.
25. Hayashi, K., et al., *Cancer metastasis directly eradicated by targeted therapy with a modified Salmonella typhimurium.* J Cell Biochem, 2009. 106(6): p. 992-8.
26. Yam, C., et al., *Monotherapy with a Tumor-Targeting Mutant of S. typhimurium Inhibits Liver Metastasis in a Mouse Model of Pancreatic Cancer.* J Surg Res, 2009.
27. Zhao, M., et al., *Monotherapy with a tumor-targeting mutant of Salmonella typhimurium cures orthotopic metastatic mouse models of human prostate cancer.* Proc Natl Acad Sci USA, 2007. 104(24): p. 10170-4.
28. Hoiseth, S. K. and B. A. Stocker, *Aromatic-dependent Salmonella typhimurium are non-virulent and effective as live vaccines.* Nature, 1981. 291(5812): p. 238-9.
29. Forbes, N. S., et al., *Sparse initial entrapment of systemically injected Salmonella typhimurium leads to heterogeneous accumulation within tumors.* Cancer Res, 2003. 63(17): p. 5188-93.
30. Leschner, S., et al., *Tumor invasion of Salmonella enterica serovar Typhimurium is accompanied by strong hemorrhage promoted by TNF-alpha.* PLoS One, 2009. 4(8): p. e6692.
31. Loessner, H., et al., *Remote control of tumour-targeted Salmonella enterica serovar Typhimurium by the use of L-arabinose as inducer of bacterial gene expression in vivo.* Cell Microbiol, 2007. 9(6): p. 1529-37.
32. Royo, J. L., et al., *In vivo gene regulation in Salmonella spp. by a salicylate-dependent control circuit.* Nat Methods, 2007. 4(11): p. 937-42.
33. Westphal, K., et al., *Containment of tumor-colonizing bacteria by host neutrophils.* Cancer Res, 2008, 68(8): p. 2952-60.
34. Clairmont, C., et al., *Biodistribution and genetic stability of the novel antitumor agent VNP20009, a genetically modified strain of Salmonella typhimurium.* J Infect Dis, 2000. 181(6): p. 1996-2002.
35. Friedlos, F., et al., *Attenuated Salmonella targets prodrug activating enzyme carboxypeptidase G2 to mouse melanoma and human breast and colon carcinomas for effective suicide gene therapy.* Clin Cancer Res, 2008. 14(13): p. 4259-66.
36. Jia, L. J., et al., *Oral delivery of tumor-targeting Salmonella for cancer therapy in murine tumor models.* Cancer Sci, 2007. 98(7): p. 1107-12.
37. Heimann, D. M. and S. A. Rosenberg, *Continuous intravenous administration of live genetically modified salmonella typhimurium in patients with metastatic melanoma.* Journal of immunotherapy, 2003. 26(2): p. 179-80.
38. Toso, J. F., et al., *Phase I study of the intravenous administration of attenuated Salmonella typhimurium to patients with metastatic melanoma.* J Clin Oncol, 2002. 20(1): p. 142-52.
39. Zhao, M., et al., *Tumor-targeting bacterial therapy with amino acid auxotrophs of GFP-expressing Salmonella typhimurium.* Proc Natl Acad Sci USA, 2005. 102(3): p. 755-60.
40. Song, M., et al., *ppGpp-dependent stationary phase induction of genes on Salmonella pathogenicity island 1,* J Biol Chem, 2004. 279(33): p. 34183-90.
41. Arrach, N., et al., *High-throughput screening for salmonella avirulent mutants that retain targeting of solid tumors.* Cancer Res, 2010. 70(6): p. 2165-70.
42. Crack, J., et al, *Influence of the Environment on the $[4Fe-4S]^{2+}$ to $[2Fe-2S]^{2+}$ Cluster Switch in the Transcriptional Regulator FNR.* J. AM. CHEM. SOC., 2008. 130: p. 1749-1758.
43. Mengesha, A., et al., *Development of a Flexible and Potent Hypoxia-Inducible Promoter for Tumor-Targeted Gene Expression in Attenuated Salmonella.* Cancer Biology & Therapy, 2006. 5(9): p. 1120-1128.
44. Boysen, A., et al., *Translational regulation of gene expression by an anaerobically induced small non-coding RNA in Escherichia coli.* J Biol Chem, 2010. 285(14): p. 10690-702.
45. Rainey, P. B. and G. M. Preston, *In vivo expression technology strategies: valuable tools for biotechnology.* Curr Opin Biotechnol, 2000. 11(5): p. 440-4,
46. Zhang, N., et al., *5-Fluorouracil: mechanisms of resistance and reversal strategies.* Molecules, 2008. 13(8): p. 1551-69.
47. Clarimont, C., et al., *Biodistribution and genetic stability of the novel antitumor agent VNP20009, a genetically modified strain of Salmonella typhimurium.* J. Infect. Dis., 2000. 181: p. 1996-2000.
48. Toso, J., V. Gill, and P. Hwu, *Phase I study of the intravenous administration of attenuated Salmonella typhimurium to patients with metastatic melanoma,* J. Clin. Oncol, 2002. 20: p. 142-152.
49. Lesebner, S. and S. Weiss, *Salmonella-allies in the fight against cancer.* J. Mol. Med., 2010. 88: p. 763-773.
50. Heap, J. T., et al., *The ClosTron: Mutagenesis in Clostridium refined and streamlined.* J Microbiol Methods, 2010, 80(1): p. 49-55.
51. Yu, B., et al., *A method to generate recombinant Salmonella typhi Ty21a strains expressing multiple heterologous genes using an improved recombinant strategy.* Appl Microbiol Biotechnol., 2011. 91: p. 177-188.
52. Datta, S., N. Costantino, and D. L. Court, *A set of recombinant plasmids for gram-negative bacteria.* Gene, 2006. 379: p. 109-15.
53. *Guidelines for Endpoints in Animal Study Proposals, ARAC.* 2005.
54. Man, K., et al., *Suppression of liver tumor growth and metastasis by adiponectin in nude mice through inhibition of tumor angiogenesis and downregulation of Rho kinase/IFN-inducible protein 10/matrix metalloproteinase 9 signaling.* Clin Cancer Res, 2010. 16: p. 967-977.
55. M. Laschke, B. V., M. Menger, *THE DORSAL SKINFOLD CHAMBER: WINDOW INTO THE DYNAMIC INTERACTION OF BIOMATERIALS WITH THEIR SURROUNDING HOST TISSUE.* European Cells and Materials, 2011, 22(147-167).
56. S. Hak, N. R., O. Haraldseth, C. Davies, *Intravital microscopy in window chambers: a unique tool to study tumor angiogenesis and delivery of nanoparticles.* Angiogenesis 2010, 13: p. 113-130.

What is claimed is:

1. A method of making modified facultative anaerobic *Salmonella typhimurium* into an obligate anaerobe, wherein said facultative anaerobic *Salmonella typhimurium* comprise a strictly hypoxia regulated essential gene expressing cassette, wherein said cassette comprises: (a) a hypoxia conditioned promoter pepT activated by FNR and comprising an FNR binding site that is operatively linked to an essential gene that encodes an enzyme essential for cell wall formation; and (b) further comprises an antisense promoter sodA that is negatively regulated by FNR, and said obligate anaerobe reduces the growth of a solid breast or liver tumor when administered in vivo.

2. The method of claim 1, wherein the obligate anaerobe is induced in the absence of diaminopimelic acid (DAP).

3. The method of claim 1, wherein the essential gene is asd.

4. The method of claim 1, wherein the hypoxia conditioned promoter is a forward anaerobic inducible promoter, and the antisense promoter is a reverse aerobic promoter.

5. The method of claim 4, wherein the forward anaerobic inducible promoter is ansB or fdhF.

6. The method of claim 1, wherein the strictly hypoxia regulated essential gene expressing cassette is chromosome-based.

\* \* \* \* \*